(12) United States Patent
Matsuo et al.

(10) Patent No.: US 11,958,970 B2
(45) Date of Patent: Apr. 16, 2024

(54) DENTAL CUT PROCESSING RESIN-BASED BLOCK

(71) Applicant: Tokuyama Dental Corporation, Taito-ku (JP)

(72) Inventors: Takuma Matsuo, Tsukuba (JP); Hironobu Akizumi, Tsukuba (JP)

(73) Assignee: Tokuyama Dental Corporation, Taito-ku (JP)

( * ) Notice: Subject to any disclaimer, the term of this patent is extended or adjusted under 35 U.S.C. 154(b) by 850 days.

(21) Appl. No.: 17/041,045

(22) PCT Filed: Mar. 28, 2019

(86) PCT No.: PCT/JP2019/013880
§ 371 (c)(1),
(2) Date: Sep. 24, 2020

(87) PCT Pub. No.: WO2019/189698
PCT Pub. Date: Oct. 3, 2019

(65) Prior Publication Data
US 2021/0095113 A1  Apr. 1, 2021

(30) Foreign Application Priority Data
Mar. 30, 2018 (JP) .................. 2018-066864

(51) Int. Cl.
| | |
|---|---|
| C08L 63/00 | (2006.01) |
| A61C 5/70 | (2017.01) |
| A61C 13/00 | (2006.01) |
| A61C 13/08 | (2006.01) |
| A61C 13/087 | (2006.01) |
| A61K 6/887 | (2020.01) |
| A61K 6/891 | (2020.01) |
| C08K 7/18 | (2006.01) |
| C08L 33/08 | (2006.01) |
| C08L 37/00 | (2006.01) |

(52) U.S. Cl.
CPC ............ *C08L 63/00* (2013.01); *A61C 5/70* (2017.02); *A61C 13/0003* (2013.01); *A61C 13/0022* (2013.01); *A61C 13/082* (2013.01); *A61C 13/087* (2013.01); *A61K 6/887* (2020.01); *A61K 6/891* (2020.01); *C08K 7/18* (2013.01); *C08L 33/08* (2013.01); *C08L 37/00* (2013.01); *C08K 2201/005* (2013.01); *Y10T 428/269* (2015.01)

(58) Field of Classification Search
CPC .......... C08L 63/00; C08L 33/08; C08L 37/00; A61C 5/70; A61C 13/0003; A61C 13/082; A61C 13/087; A61C 13/0024; A61K 6/887; A61K 6/891; A61K 6/16; A61K 6/17; A61K 6/816; A61K 6/831; A61K 6/84; C08K 7/18; C08K 2201/005; Y10T 428/269
USPC ....................................... 524/492
See application file for complete search history.

(56) References Cited

U.S. PATENT DOCUMENTS

| | | |
|---|---|---|
| 8,946,318 B2 | 2/2015 | Akizumi et al. |
| 2017/0151041 A1 | 6/2017 | Goto et al. |
| 2018/0303721 A1 | 10/2018 | Akizumi et al. |

FOREIGN PATENT DOCUMENTS

| | | |
|---|---|---|
| EP | 1 005 911 A1 | 6/2000 |
| EP | 2 548 916 B1 | 12/2016 |
| JP | 2017-105764 A | 6/2017 |
| JP | 2017-149650 A | 8/2017 |
| RU | 2 275 183 C2 | 4/2006 |
| RU | 2 621 624 C2 | 6/2017 |
| WO | WO 2012/128167 A1 | 9/2012 |
| WO | WO 2017/069274 A1 | 4/2017 |

OTHER PUBLICATIONS

Combined Russian Office Action and Search Report dated May 25, 2022 in Russian Patent Application No. 2020131607 (with English translation and Translation of Category of Cited Documents), citing references AO and AP therein, 15 pages.

International Search Report dated Jun. 11, 2019 in PCT/JP2019/013880 filed Mar. 28, 219, citing documents AA-AC and AO-AR therein, 1 page.

Extended European Search Report dated Nov. 5, 2021, in European Patent Application No. 19775878.2, citing documents AO, AP and AX therein, 9 pages.

Olson, E., "Particle Shape Factors and Their Use in Image Analysis—Part 1:Theory", Journal of GXP Compliance, Jan. 1, 2011, vol. 15, No. 3, XP055305841, pp. 85-96.

*Primary Examiner* — Hannah J Pak
(74) *Attorney, Agent, or Firm* — Oblon, McClelland, Maier & Neustadt, L.L.P.

(57) ABSTRACT

A resin block suitable for dental cutting work may include a resin matrix (A) and spherical filler (B) whose average particle size ranges from 230 to 1000 nm. When 10 mm thick and measured with a colorimeter, the lightness (V) is less than 5.0 and the saturation (C) is less than 2.0 in a Munsell color system of colored light on a black background and a white background. When 1 mm thick, the lightness (V) is less than 5.0 and the saturation (C) is 0.05 or more on a black background, but on a white background, the lightness (V) is 6.0 or more and the saturation (C) is less than 2.0 for Munsell colored light. Resin blocks can be used for dental restoration such that dental prostheses produced from the block not using a pigment/dye are compatible with natural teeth color tone, and the color tone compatibility endures.

6 Claims, No Drawings

DENTAL CUT PROCESSING RESIN-BASED BLOCK

TECHNICAL FIELD

The present invention relates to a resin block for dental cutting work for producing a dental prosthesis that is simple and has excellent aesthetic appearance.

In dental treatment, as a method for producing a dental prosthesis such as an inlay, an onlay, a crown, a bridge, and an implant upper structure, a cutting method that uses a dental CAD/CAM system is known. The CAD/CAM system is a system that uses a computer to design a dental prosthesis based on three-dimensional coordinate data and uses a cutting machine to produce the prosthesis. As a cutting material, various materials such as glass ceramics, zirconia, titanium and resins are used. As a dental cutting resin material, there are provided block-shaped or disc-shaped cured products that are prepared by curing a curable composition containing an inorganic filler such as silica, a polymerizable monomer such as a methacrylate resin, and a polymerization initiator. Dental cutting resin materials have been attracting attention from the viewpoints of high workability, aesthetics and strength, and various material have been proposed.

Dental treatment requires to give an appearance that is as close as possible to the color tone of natural teeth, but in order to meet such aesthetic requirements, in many cases, it is not always sufficient to produce a block body composed of a single component by cutting, and heretofore, many block bodies for cutting work each composed of multilayer color tones have been proposed.

For example, PTL 1 describes an invention relating to a resin block for dental cutting work, which is composed of a plurality of layers having different color tones and transparency (contrast ratio), specifically saying that when two or three layers in the block are made to satisfy a specific relationship between color tone and transparency (contrast ratio), the resultant block can have the same ivory color and enamel color as those of natural teeth and the boundary between the constituent layers therein can be inconspicuous.

PTL 2 describes an invention relating to a curable composition useful as a dental filling and restoring material, which has excellent color tone compatibility with natural teeth without using a pigment or dye, specifically describing a dental filling and restoring material which uses a spherical filler having a particle size falling within a predetermined range and which gives a cured product whose appearance is in harmony with natural teeth and the harmony thereof with natural teeth continues for a long time. However, in the case of repairing a large cavity that requires inlay repair or the like in a molar portion to which occlusal pressure is applied, the curable composition has a concern in point of mechanical strength.

CITATION LIST

Patent Literature

PTL 1: JP 2017-105764 A
PTL 2: WO2017/069274

SUMMARY OF INVENTION

Technical Problem

PTL 1 mentioned above relates to a color tone and a layer structure of a block used in a dental CAD/CAM system. However, since there are individual differences in the color tone of natural teeth, in the prior art, it is necessary to manufacture a block composed of multiple layers having different color tones and transparency (contrast ratio), and in addition, in order to match the difference in color tone owing to individual differences, it is necessary to manufacture multiple types of blocks with different color tones, which makes the block manufacturing technology complicated and difficult. Further, since the color tone and the transparency of the block and each layer structure are controlled using a pigment and a dye, there may occur discoloration or color fading with time, therefore causing another problem that the color tone of the block could no more match that of natural teeth.

PTL 2 relates to a curable composition that does not cause discoloration or color fading with time and can provide a cured product having good color tone compatibility with natural teeth. The curable composition described in PTL 2 is a dental filling and restoring material, and the color tone compatibility thereof is evaluated when the thickness is 2 mm or less, but whether or not a thicker one such as a prosthesis produced by cutting has the color tone compatibility is not described and is unclear.

Accordingly, an object of the present invention is to provide a resin block for dental cutting work which is not required to be composed of blocks having different color tones or is not required to have a layered structure having plural different color tones, which enables dental restoration in such a manner that the appearance of the dental prosthesis made from the block without using a pigment or a dye is compatible with the color tone of natural teeth, and which realizes continuing harmony in the color tone between the dental prosthesis made from the block and natural teeth.

Solution to Problem

In consideration of the above-mentioned problems, the present inventors have continued assiduous studies. As a result, the present inventors have found that a dental prosthesis made from a resin block for dental cutting work, which contains spherical particles having a specific particle size and which exhibits a specific color tone behavior in such a way that, when having a thickness of 10 mm, the resin block develops a reddish color tone on a black background and a white background and has the same color tone, but when having a thickness of 1 mm, it develops a reddish color tone on a black background and does not develop any color on a white background and is substantially white, has excellent color tone compatibility with natural teeth and can solve the above-mentioned problems, and have completed the present invention.

Specifically, the resin block for dental cutting work of the present invention is a resin block for dental cutting work containing a resin matrix (A) and a spherical filler (B) whose average particle size falls within a range of 230 nm to 1000 nm, which is such that, when having a thickness of 10 mm and as measured with a colorimeter, the lightness (V) is less than 5.0 and the saturation (C) is less than 2.0 as measured values in a Munsell color system of the colored light on a black background and a white background, and is such that, when having a thickness of 1 mm and as measured with a colorimeter, the lightness (V) is less than 5.0 and the saturation (C) is 0.05 or more as measured values in a Munsell color system of the colored light on a black background, but on a white background, the lightness (V) is 6.0 or more and the saturation (C) is less than 2.0 as measured values in a Munsell color system of the colored light.

For obtaining the resin block for dental cutting work, 90% or more of the individual particles constituting the spherical filler (B) are present within a range of the average particle size±5%, and the resin matrix (A) and the spherical filler (B) each are selected so as to satisfy a requirement (X1) represented by the following expression (1):

$$nP<nF \quad (1)$$

where nP represents a refractive index of the resin matrix (A) at 25° C., and nF represents a refractive index of the spherical filler (B) at 25° C.

In the resin block for dental cutting work, the average particle size of the spherical filler (B) preferably falls within a range of 240 nm to 500 nm. The resin block for dental cutting work is favorable for repairing a cavity in which a dentin portion is located in a deep surface. Here, the deep surface means the bottom of the repairing cavity and the side wall below the surface where enamel is located.

More preferably, the resin block for dental cutting work contains inorganic particles (C) having an average particle size of less than 100 nm.

The present invention also provides a method for producing a resin block for dental cutting work that contains a resin matrix (A) and a spherical filler (B) whose average particle size falls within a range of 230 nm to 1000 nm; the method including polymerizing a curable composition, which contains a polymerizing monomer, a spherical filler (B) whose average particle size falls within a range of 230 nm to 1000 nm and a polymerization initiator, and in which 90% or more of the individual particles constituting the spherical filler (B) are present within a range of the average particle size±5%, and the polymerizing monomer and the spherical filler (B) each are selected so as to satisfy a requirement (X2) represented by the following expression (2):

$$nPm<nF \quad (2)$$

where nPm represents a refractive index at 25° C. of a polymer obtained through polymerization of the polymerizing monomer, and nF represents a refractive index of the spherical filler (B) at 25° C.; and in which the resin block for dental cutting work is such that, when having a thickness of 10 mm and as measured with a colorimeter, the lightness (V) is less than 5.0 and the saturation (C) is less than 2.0 as measured values in a Munsell color system of the colored light on a black background and a white background, and is such that, when having a thickness of 1 mm and as measured with a colorimeter, the lightness (V) is less than 5.0 and the saturation (C) is 0.05 or more as measured values in a Munsell color system of the colored light on a black background, but on a white background, the lightness (V) is 6.0 or more and the saturation (C) is less than 2.0 as measured values in a Munsell color system of the colored light.

Advantageous Effects of Invention

The resin block for dental cutting work of the present invention is such that the dental prosthesis to be formed of it can color differently in accordance with the color tone of natural teeth that varies depending on an individual difference and on a repairing portion, and therefore, the resin block is not required to have a laminated structure of plural layers having different color tones and a resin block for dental cutting work can be produced in a simplified manner. In addition, the dental prosthesis formed of the resin block for dental cutting work of the present invention makes it possible to repair in such a manner that the appearance thereof is compatible with the color tone of natural teeth irrespective of the size and the depth of the cavity to be repaired, and further, as utilizing interfering light, the resin block is free from color fading and discoloration, and therefore the harmony between the resultant cured product and natural teeth can continue in repairing with the resin block.

DESCRIPTION OF EMBODIMENTS

The resin block for dental cutting work of the present invention is a block having as one component a resin matrix, which is used in producing a dental prosthesis with a cutting machine based on the three-dimensional coordinate data acquired on a computer. The shape and the size are not limited, and any one having a shape and a size according to the intended purpose may be selected. The shape is arbitrarily selected from a rectangular parallelepiped shape, a cylindrical shape, a disk shape and the like according to the intended use and the cutting device used. As for the size, for example, in the case of a rectangular parallelepiped shape, the length of one side is usually selected from the range of 5 mm to 150 mm, and preferably 10 mm to 150 mm. The volume is usually selected from the range of 1.8 $cm^3$ to 200 $cm^3$.

The resin block for dental cutting work of the present invention (hereinafter sometimes simply referred to as a block) contains a resin matrix (A) and a spherical filler (B) having an average particle size within a range of 230 nm to 1000 nm. The average particle size of the spherical filler (B) means an average primary particle size.

The resin block for dental cutting work of the present invention has a specific color tone behavior such that, when measured at a thickness of 10 mm with a colorimeter, the lightness (V) is less than 5.0 and the saturation (C) is less than 2.0 as measured values in a Munsell color system of the colored light on a black background (a base with a lightness of 1 according to the Munsell color system) and a white background (a base with a lightness of 9.5 according to the Munsell color system), and is such that, when measured at a thickness of 1 mm with a colorimeter, the lightness (V) is less than 5.0 and the saturation (C) is 0.05 or more as measured values in a Munsell color system of the colored light on a black background, but on a white background, the lightness (V) is 6.0 or more and the saturation (C) is less than 2.0 as measured values in a Munsell color system of the colored light.

By controlling the measured values of the colored light of the resin block for dental cutting work on a black background and a white background in a Munsell color system at a thickness of 10 mm and a thickness of 1 mm, in the manner as above, the color tone compatibility of the resin block with natural teeth is bettered. The resin block for dental cutting work of the present invention can be applied to repairing of cavities of various sizes, and even when applied to repairing of a relatively large cavity, the color tone compatibility of the resin block is still good.

Measured at a thickness of 1 mm, when the lightness on a black background is more than 5.0 and when the saturation is less than 0.05, the resin block is nontransparent and is white with no coloration, and therefore, when the resin block of the type is put on a tooth having a high saturation (A4 or so), a good color tone compatibility could not be attained. Measured at a thickness of 1 mm, when the lightness on a white background is less than 6.0 and the saturation is 2.0 or more, coloration on a white background can be visually confirmed, and therefore, when the resin block of the type is put on a tooth having a low saturation (A1 or so), a good color tone compatibility could not be attained.

Preferably, the lightness (V) of the colored light on a black background of the resin block for dental cutting work, as cut to have a thickness of 1 mm, is 4.5 or less, more preferably 4.0 or less. Preferably, the saturation (C) of the colored light on a back background of the resin block for dental cutting work, as cut to have a thickness of 1 mm, is 0.07 or more, more preferably 0.09 or more. Preferably, the lightness (V) of the colored light on a white background of the resin block for dental cutting work, as cut to have a thickness of 1 mm, is 6.5 or more, more preferably 7.0 or more. Preferably, the saturation (C) of the colored light on a white background of the resin block for dental cutting work, as cut to have a thickness of 1 mm, is 1.5 or less, more preferably 1.2 or less.

The average particle size of the spherical filler (B) to be contained is 230 nm to 1000 nm, and therefore the colored light on a black background is yellow to reddish, and specifically, the hue (H) of the measured values of the colored light, as measured according to a Munsell color system at a thickness of 1 mm, falls within a range of 0 P or more and less than 10 P, 0 RP or more and less than 10 RP, 0 R or more and less than 10 R, 0 YR or more and less than 10 YR, 0 Y or more and less than 10 Y, and 0 GY or more and less than 10 GY. Preferably, it falls within a range of 0 P or more and less than 10 P, 0 RP or more and less than 10 RP, 0 R or more and less than 10 R, 0 YR or more and less than 10 YR, and 0 Y or more and less than 10 Y, more preferably within a range of 0 RP or more and less than 10 RP, 0 R or more and less than 10 R, 0 YR or more and less than 10 YR, and 0 Y or more and less than 10 Y.

Regarding such a reddish color hue property on a black background, all the lightness, the saturation and the hue can be in good harmony, even when the ambient environment changes variously from a reddish yellow to a reddish brown so far as the area around the dental prosthesis obtained by working the resin block for dental cutting work of the present invention is in an environment where it presents a reddish color. Specifically, in the case where the chromaticity (hue and saturation) of the background (base environment) is high, an external light such as an irradiated light is absorbed by the background having a high chromaticity, and the other light than the colored light from the block (or a dental prosthesis produced by working the block) is retarded, and therefore the colored light can be observed. On the other hand, in the case where the chromaticity of a tooth of the background (base environment) is low, an external light such as an irradiated light is scattered by the background having a low chromaticity and the scattered light is stronger than the colored light from the block (or a dental prosthesis produced by working the block), and therefore the colored light is canceled to weaken. Accordingly, the resin block for dental cutting work of the present invention produces a strong colored light to the base environment having a high chromaticity but produces a weak colored light to the base environment having a low chromaticity, and consequently, the resin block exhibits an effect of widely according with various reddish ambient environments.

The resin block for dental cutting work having such a specific color tone behavior can be obtained by using a spherical filler (B) having a specific average particle size and having a narrow particle size distribution, and by selecting a resin matrix (A) and the spherical filler (B) so that the refractive indices thereof could satisfy a requirement (X1) represented by the following expression (1):

$$nP < nF \qquad (1)$$

wherein nP represents a refractive index of the resin matrix (A) at 25° C., and nF represents a refractive index of the spherical filler (B) at 25° C., as described hereinunder.

As shown by the expression (1), the resin block for dental cutting work of the present invention is such that the relationship between the refractive indices of the resin matrix (A) and the spherical filler (B) therein is nP<nF. In the case where the refractive index of the spherical filler (B) is high and the refractive index of the resin matrix is low, a colored light may be expressed by interference or scattering, but in an opposite case, a light having a short wavelength can be readily interfered or scattered so that the resultant colored light is to have a shortened wavelength and becomes blueish, that is, the resin block of the type would have a poor color tone compatibility with repairing sites having various color tones.

The resin block for dental cutting work of the present invention is characterized by expressing a colored light through a phenomenon of interference and scattering, and whether or not the resin block can express a colored light can be confirmed by measuring the spectral reflectivity characteristics thereof under two conditions of a black background and a white background, using a colorimeter. On a black background in the case where the above-mentioned requirement (X1) is satisfied, a light having a specific visible spectrum (380 to 780 nm) can be clearly confirmed as a specific reflection spectrum in accordance with the colored light, but on a white background, a substantially uniform reflectivity is shown in a substantially entire range of the visible spectrum, that is, a light of a visible spectrum is not confirmed and the resin block is substantially colorless. This is because, on a black background, an external light (for example, C light source, D65 light source) is absorbed or blocked and the colored light by interference is emphasized. On the other hand, on a white background, it is considered that a scattered reflection light of an external light is strong and the colored light by interference could hardly be observed.

The constituent components of the resin block for dental cutting work of the present invention are described below.

<Resin Matrix (A)>

The resin matrix (A) in the present invention is a component that plays a role of a dispersion medium for dispersing the spherical filler (B). With no specific limitation, the resin matrix may be any resin satisfying the above-mentioned requirement (X1), and any of a thermoplastic resin and a thermosetting resin is usable. From the viewpoint of aesthetics of dental prostheses, a resin having a high transparency is preferred. Specifically, acrylic resins such as polymethyl methacrylate, polyester resins such as polystyrene, polyamide, polycarbonate and polyethylene terephthalate, methyl methacrylate-butadiene-styrene resins, acrylonitrile-butadiene-styrene resins, cycloolefin polymers, epoxy resins, oxetane resins, or copolymers thereof are favorably used. Especially from the viewpoint of safety, high transparency and easiness in refractive index control, acrylic resins, epoxy resins and oxetane resins are favorably used.

<Spherical Filler (B)>

A dental restorative material contains various fillers such as an inorganic powder and an organic powder. The resin block for dental cutting work of the present invention contains a spherical filler (B) having an average primary particle size of 230 to 1000 nm for the purpose of expressing a colored light by interference. The resin block for dental cutting work of the present invention is characterized in that the constituent filler is spherical and that the particle size distribution thereof is narrow. A colored light by interference forms in a part where the constituent spherical filler is relatively regularly accumulated, and a colored light by scattering forms in a part where the constituent spherical filler is randomly dispersed. Accordingly, when the spherical filler (B) that constitutes the resin block for dental cutting work of the present invention has a uniform spherical shape and the particle size distribution thereof is narrow, a colored light is formed by interference. As opposed to this, when an irregularly shaped filler produced by grinding is used, the shape thereof is not uniform and the particle size distribution thereof is broad, and therefore the filler could not be accumulated regularly and a colored light by interference could not be formed.

The wording used in the present invention "the spherical filler is accumulated relatively regularly" means that the spherical filler is uniformly dispersed in the resin matrix component in a state to have an isotropic structure aligned in accordance with a certain fixed order.

As described above, it is important that the spherical filler (B) has an average primary particle size of 230 to 1000 nm, and that 90% (by number) or more of the individual particles constituting the spherical filler (B) are present within a range of the average particle size±5%. Namely, the above means that the spherical filler (B) is composed of plural primary particles, and 90% by number or more of all the primary particles thereof exist within a range of the average particle size±5% of the plural primary particles. A range of the average particle size±5% means a range of a particle size of 0.95×d to 1.05×d where d represents the average particle size. When 90% by number or more of the individual particles constituting the spherical filler (B) exist within a range of the average particle size±5%, the intensity of the colored light can be strong, and the color tone compatibility with natural teeth betters. Expression of a colored light by interference results from diffraction interference according to Bragg's condition to emphasize a light having a specific wavelength, and when particles having the above-mentioned particle size are blended, the resin block for dental cutting work can come to express a yellow to reddish colored light according to the particle size of the particles blended therein.

From the viewpoint of attaining an excellent color tone compatibility with a tooth substance for the cavity formed from enamel to dentin, the wavelength of the colored light is preferably 550 to 770 nm, more preferably 580 to 760 nm. Falling within the range, the colored light from the resin block for dental cutting work can be yellow to reddish and therefore the resin block has a good color tone compatibility with natural teeth. The wavelength of the colored light is a wavelength of the colored light from the resin block for dental cutting work having a thickness of 1 mm on a black background. The wavelength of the colored light is a maximum point of the reflectivity in measuring the spectral reflectivity with a colorimeter, and in detail, can be measured according to the method described in the section of Examples.

From the viewpoint of further increasing the effect of colored light expression by interference, the average primary particle size of the spherical filler (B) is favorably 230 to 800 nm, more favorably 240 to 500 nm, even more favorably 260 to 350 nm, further more favorably 260 to 290 nm, still further more preferably 260 to 275 nm. In the case where a spherical filler having a particle size falling within a range of 150 nm or more and less than 230 nm, the resultant colored light is blue, and the color tone compatibility thereof with a tooth substance is often poor and, further, in the case where a spherical filler smaller than 100 nm is used, an interference phenomenon of a visible light hardly occurs. On the other hand, in the case where a spherical filler larger than 1000 nm is used, an interference phenomenon of light could be expected, but in the resin block for dental cutting work of the present invention, such a large filler is unfavorable since the polishing or cutting performance of the resin block for dental cutting work may worsen.

The resin block for dental cutting work of the present invention develops various colored lights on a black background depending on the particle size of the spherical filler (B). Therefore, the average primary particle size of the spherical filler (B) may be determined within a range of 230 to 1000 nm so that desired color light can be obtained. When spherical particles with a particle size in a range of 230 nm to 260 nm are used, a yellowish colored light is given, and is useful for restoration of teeth in the B-type (red-yellow) category of a shade guide "VITAPAN Classical (registered trademark)". When spherical fillers with a particle size in a range of 260 nm to 350 nm are used, a reddish colored light is given, and is useful for restoration of teeth in the A-type (red-brown) category of the shade guide "VITAPAN Classical (registered trademark)". Since the hue of dentin is often such a reddish hue, in the present invention, in a mode in which spherical fillers having an average primary particle size of 260 nm to 350 nm are used as above, the resin block most favorably secures such a broad and good compatibility with restoration of teeth in various color tones.

It is important that the primary particle size of the spherical filler (B) falls within the above-mentioned average range.

In the present invention, the average particle size of the spherical filler (B) is an average value calculated as follows. A picture of the powder of the spherical filler is taken with a scanning electronic microscope, and the number of all the particles (30 particles or more) seen in a unit field of view of the picture and the primary particle size (maximum diameter) of all the particles are measured, and from the resultant measured values, the average value is calculated according to the following equation.

$$\bar{x} = \frac{\sum_{i=1}^{n} x_i}{n} \text{ (number average)}$$

(n: number of particles, $x_i$: primary particle size (maximum diameter) of i'th particle)

In the present invention, the proportion (%) of particles falling within a range of the average particle size±5% of the spherical filler (B) is calculated as follows. Among all the particles (30 particles or more) seen in a unit field of view of the picture, the number of the particles having a primary particle size (maximum diameter) not falling within a range of the average particle size±5% as determined in the above is counted, and the counted value is subtracted from the number of all the particles to give the number of particles falling within a range of the average particle size±5% in the unit field of view in the picture, and the intended proportion of the particles is calculated according to the following equation:

Proportion (%) of particles falling within a range of the average particle size±5% of the spherical filler (B)=[(number of particles within the particle size range of the average particle size±5% in the unit field of view of the scanning electron microscopic picture)/(number of all the particles in the unit field of view of the scanning electron microscopic picture)]×100

Here, regarding the spherical shape thereof, the spherical filler may be a nearly spherical one and is not always needed to be a completely true sphere. Generally, a picture of particles is taken with a scanning electronic microscope, and the maximum diameter of the individual particles (30 particles or more) within the unit field of view therein is measured, and the average evenness is calculated by dividing the particle size in the direction perpendicular to the maximum diameter by the maximum diameter. The thus-measured average evenness of the spherical filler as referred to herein may be 0.6 or more, preferably 0.8 or more.

The resin block for dental cutting work of the present invention may contain the spherical filler (B) in any form so far as the above-mentioned requirement is satisfied. For example, the spherical filler (B) may be a powdery spherical filler (B) consisting of a spherical filler (B), or may be an organic-inorganic composite filler (B2) containing an inorganic spherical filler (B). A combination of these is also employable. The organic-inorganic filler (B2) may be prepared, for example, by mixing an aggregate prepared by aggregating an inorganic spherical filler (B) and a polymerizing monomer, then polymerizing and curing the resultant mixture and grounding the cured product.

The spherical filler (B) using the above-mentioned powder as such may be referred to as a spherical filler (B1), and the organic-inorganic composite filler containing an inorganic spherical filler (B) may be referred to as an organic-inorganic composite filler (B2).

The resin block for dental cutting work of the present invention may contain a powdery spherical filler (B1) consisting of a spherical filler (B) and an organic-inorganic composite filler (B2). The resin block for dental cutting work of the type is favorable since the mechanical strength thereof can be effectively high.

In the case where a powdery spherical filler (B1) and an organic-inorganic composite filler (B2) are used together, the powdery spherical filler (B1) and the inorganic spherical filler (B) in the organic-inorganic composite filler (B2) may be the same spherical filler or may be different spherical fillers, but from the viewpoint of bettering color tone compatibility, preferably the two are the same spherical filler.

As the spherical filler (B), any one usable as a component of an ordinary curable composition for dental use can be used with no limitation. The spherical filler (B) may be an organic spherical filler, or may be an inorganic spherical filler, but from the viewpoint that, by blending in the block of the present invention, the resultant block can have an increased mechanical strength and is given glossiness close to that of natural teeth, an inorganic spherical filler is preferred. Specifically, the inorganic spherical filler includes inorganic powders of amorphous silica, silica-titanium group element oxide-based composite oxide particles (e.g., silica-zirconia, silica-titania), quartz, alumina, barium glass, strontium glass, lanthanum glass, fluoroaluminosilicate glass, ytterbium fluoride, zirconia, titania, or colloidal silica.

Among these, silica-titanium group element oxide-based composite oxide particles are preferred since the refractivity of the filler can be readily controlled.

In the present invention, the silica-titanium group element oxide-based composite oxide particles are of a composite oxide of silica and a titanium group (Periodic Table Group IV element) oxide, and include silica-titania, silica-zirconia, and silica-titania-zirconia. Among these, from the viewpoint that the refractive index of the filler can be controlled and that the filler can give a high X-ray imperviousness, silica-zirconia is preferred. Though not specifically limited, the compounding ratio is, from the viewpoint of imparting sufficient X-ray imperviousness and of controlling the refractive index to fall within the preferred range mentioned below, preferably, the silica content is 70 to 95 mol %, and the titanium group oxide content is 5 to 30 mol %. In the case of silica-zirconia, the refractive index thereof can be varied in any manner by changing the compounding ratio.

The silica-titanium group element oxide-based composite oxide particles may be further compounded with only a small amount of any other metal oxide than silica and titanium group element oxides. Specifically, an alkali metal oxide such as sodium oxide and lithium oxide may be incorporated in an amount of 10 mol % or less.

A method for producing such silica-titanium group element oxide-based composite oxide particles is not specifically limited. For the purpose of obtaining the specific spherical filler for use in the present invention, for example, a so-called sol-gel method is favorably employed, in which a mixed solution of a hydrolyzable organic silicon compound and a hydrolyzable organic titanium group metal compound is added to an alkaline solvent, and hydrolyzed to precipitate a reaction product.

The silica-titanium group element oxide-based composite oxide particles may be surface-treated with a silane coupling agent. By surface treatment with a silane coupling agent, the interface strength of the powders to the resin matrix (A) can be bettered. Examples of a typical silane coupling agent include an organic silicon compound such as γ-methacryloyloxyalkyltrimethoxysilane, and hexamethyldisilazane. The surface treatment amount with the silane coupling agent is not specifically limited, and an optimum value thereof may be determined by previously confirming the mechanical properties of the resultant resin block for dental cutting work by experiments. An example of the preferred range of the agent is 0.1 to 15 parts by mass relative to 100 part by mass of the spherical filler (B).

As mentioned above, a colored light by interference or scattering that expresses a good color tone compatibility to natural teeth can be obtained when the resin matrix (A) and the spherical filler (B) satisfy the following expression (1):

$$nP<nF \qquad (1)$$

wherein nP represents a refractive index of the resin matrix (A) at 25° C., and nF represents a refractive index of the spherical filler (B) at 25° C.

Specifically, the refractive index of the spherical filler (B) is higher than the refractive index of the resin matrix (A). Preferably, a difference between the refractive index nF (25° C.) of the spherical filler (B) and the refractive index nP (25° C.) of the resin matrix (A) (nF−nP) is 0.001 or more, more preferably 0.002 or more, most preferably 0.005 or more. Regarding the refractive index, when the transparency of the resin block for dental cutting work is high, a colored light is expressed more sharply, and therefore, those such that the refractive index difference (nF−nP) between the spherical filler (B) and the resin matrix (A) is 0.1 or less, more preferably 0.05 or less, and those not detracting from transparency as much as possible are preferably selected and used.

The blending amount of the spherical particles (B) in the present invention is 10 parts by mass to 1500 parts by mass relative to 100 parts by mass of the resin matrix (A). When the spherical particles (B) are blended in an amount of 10 parts by mass or more, a colored light can be better expressed by interference and scattering. In the case where the spherical particles (B) such that the refractive index difference thereof from the resin matrix (A) is more than above-mentioned 0.1 are used, the transparency of the resin block for dental cutting work lowers and the effect of expressing a colored light could not be sufficiently expressed. Taking these into consideration, the blending amount of the spherical particles (B) is preferably 50 parts by mass to 1500 parts by mass relative to 100 parts by mass of the resin matrix (A), more preferably 100 parts by mass to 1500 parts by mass.

Among the spherical filler (B), the refractive index of the silica-titanium group element oxide-based composite oxide whose refractive index is readily controlled falls within a range of 1.45 to 1.58 or so depending on the content of the silica fraction therein. Specifically, in the case where a silica-titanium group element oxide-based composite oxide is used as the spherical filler (B), the refractive index nP of the resin matrix (A) can be controlled to fall within a range of approximately 1.40 to 1.57 by so controlling the refractive index of the polymerizing monomer to be a starting material for the resin matrix (A) as to fall within the range to be mentioned below (within a range of 1.38 to 1.55), and accordingly, the spherical filler (B) can be readily selected so as to satisfy the above-mentioned requirement (X1). Specifically, a silica-titanium group element oxide-based composite oxide (for example, silica-titania or silica-zirconia) that contains an appropriate amount of a silica fraction may be used.

<Organic-Inorganic Composite Filler (B2)>

In the present invention, as mentioned above, the spherical filler (B) may be used as a powdery spherical filler (B1) as such, or an organic-inorganic composite filler (B2) may also be used. Containing an organic-inorganic composite filler (B2), the resin block for dental cutting work may have an increased mechanical strength and the property thereof as dental prostheses can be readily bettered.

The organic-inorganic composite filler (B2) contains an organic resin matrix and an inorganic spherical filler (B) dispersed in the organic resin matrix. Hereinunder, the organic resin matrix contained in the organic-inorganic composite filler (B2) is referred to as an organic resin matrix (b1), and the inorganic spherical filler (B) contained in the organic-inorganic composite filler is referred to as a spherical inorganic filler (b2).

In the case where the spherical filler (B) is used as a form of the organic-inorganic composite filler (B2), and also in the case where the organic-inorganic composite filler (B2) is added to the resin block for dental cutting work in such a manner that the refractive index difference between the spherical inorganic filler (b2) and the organic resin matrix (b1) constituting the organic-inorganic composite filler (B2), and the refractive index difference between the spherical inorganic filler (b2) and the resin matrix (A) are to satisfy the expressions (3) and (4), respectively, to be mentioned below, there occurs diffraction interference of light according to Bragg's condition of diffraction and a colored light having the same wavelength as in the case where the spherical filler (B1) having the same average primary particle size as that of the spherical inorganic filler (b2) is used singly is thereby expressed.

The spherical inorganic filler (b2) constituting the organic-inorganic composite filler (B2) may be the same as or different from the spherical filler (B1) used in the form of a powder, but like the spherical filler (B1) used in the form of a powder, the filler (b2) is spherical and has an average primary particle size falling within a range of 230 nm to 1000 nm, and it is important that 90% by number or more of the individual particles constituting the spherical inorganic filler (b2) falls within a range of the average primary particle size±5%, and further, the refractive index $nF_{b2}$ of the spherical inorganic filler (b2) satisfies the relationship between the refractive index $nM_{b1}$ of the organic resin matrix (b1) and the refractive index $nF_{b2}$ of the spherical inorganic filler (b2) represented by the following expression (3), and the relationship between the refractive index nP of the resin matrix (A) and the refractive index $nF_{b2}$ of the spherical inorganic filler (b2) represented by the following expression (4).

$$nM_{b1} < nF_{b2} \qquad (3)$$

wherein $nM_{b1}$ represents a refractive index at 25° C. of the organic resin matrix (b1) constituting the organic-inorganic composite filler (B2), and $nF_{b2}$ represents a refractive index at 25° C. of the spherical inorganic filler (b2).

$$nP < nF_{b2} \qquad (4)$$

wherein nP represents a refractive index at 25° C. of the resin matrix (A), and $nF_{b2}$ represents a refractive index at 25° C. of the spherical inorganic filler (b2) constituting the organic-inorganic composite filler (B2).

Specifically, it is important that the refractive index $nF_{b2}$ of the spherical inorganic filler (b2) is higher than the refractive index nP of the resin matrix (A) and is higher than the refractive index $nM_{b1}$ of the organic resin matrix (b1) constituting the organic-inorganic composite filler (B2).

The refractive index difference ($nF_{b2}$−nP) between the refractive index $nF_{b2}$ of the spherical inorganic filler (b2) and the refractive index nP of the resin matrix (A), and the refractive index difference ($nF_{b2}$−$nM_{b1}$) between the refractive index $nF_{b2}$ of the spherical inorganic filler (b2) and the refractive index $nM_{b1}$ of the organic resin matrix (b1) each are preferably 0.001 or more, more preferably 0.002 or more, most preferably 0.005 or more.

Also the refractive index difference ($nF_{b2}$−nP) between the refractive index $nF_{b2}$ of the spherical inorganic filler (b2) and the refractive index nP of the resin matrix (A), and the refractive index difference ($nF_{b2}$−$nM_{b1}$) between the refractive index $nF_{b2}$ of the spherical inorganic filler (b2) and the refractive index $nM_{b1}$ of the organic resin matrix (b1) each are preferably 0.1 or less, more preferably 0.05 or less so as not to detract from transparency as much as possible.

The content of the spherical inorganic filler (b2) in the organic-inorganic composite filler (B2) is preferably 30% by mass or more and 95% by mass or less. When the content in the organic-inorganic composite filler (B2) is 30% by mass or more, the block can favorably express the colored light and the mechanical strength thereof can be sufficiently increased. On the other hand, incorporating the spherical inorganic filler (b2) in an amount more than 95% by mass into the organic-inorganic composite filler (B2) is technically difficult, and in such a case, a homogeneous filler could hardly be formed. A more preferred content of the spherical inorganic filler (b2) in the organic-inorganic composite filler (B2) is 40 to 90% by mass.

Like that of the spherical filler (B1) used as a powder, the refractive index of the silica-titanium group element oxide-based composite oxide whose refractive index can be controlled with ease among the spherical inorganic filler (b2) can fall within a range of approximately 1.45 to 1.58 depending on the content of the silica fraction therein. Specifically, in the case where a silica-titanium group element oxide-based composite oxide is used as the spherical inorganic filler (b2), the refractive index nP of the resin matrix can be controlled to fall within a range of approximately 1.40 to 1.57 by presetting the refractive index of the polymerizing monomer to be a raw material for the resin matrix (A) to fall within the above-mentioned range (within a range of 1.38 to 1.55), and therefore the spherical inorganic filler (b2) can be thereby readily selected so as to satisfy the above-mentioned requirement (expression (4)). Specifically, a silica-titanium group element oxide-based composite oxide containing a suitable amount of a silica fraction (for example, silica-titania or silica-zirconia) may be used.

In the organic-inorganic composite filler (B2), any homopolymer obtained using the same polymerizing monomer as that described to be the polymerizing monomer of a raw material for the resin matrix (A) as mentioned below or any copolymer of plural kinds of such monomers is employable with no limitation for the organic resin matrix (b1). As described hereinabove, in the case where a silica-titanium group element oxide-based composite oxide whose refractive index is readily controlled is used as the spherical inorganic filler (b2), the refractive index thereof falls within a range of approximately 1.45 to 1.58 depending on the content of the silica fraction therein, and therefore the above-mentioned requirement (expression (3)) can be satisfied by controlling the refractive index $nM_{b1}$ of the organic resin matrix (b1) to fall within a range of approximately 1.40 to 1.57.

The organic resin matrix (b1) may be the same as or different from the resin matrix (A), but the refractive index difference between the refractive index $nM_{b1}$ of the organic resin matrix (b1) and the refractive index nP of the resin matrix (A) is preferably 0.005 or less from the viewpoint of the transparency of the resultant resin block for dental cutting work. When the refractive index difference is larger than 0.005, the resin block may be nontransparent and the colored light by interference would be weak. Further, from the viewpoint that light diffusibility can be given by the refractive index difference to improve the color tone compatibility between the resin block for dental cutting work and teeth, the refractive index difference is more preferably within a range of 0.001 to 0.005.

In the present invention, a method for producing the organic-inorganic composite filler (B2) is not specifically limited, for which employable is a general production method for an organic-inorganic composite filler that includes mixing a predetermined amount of each component of a spherical inorganic filler (b2), an organic resin matrix (b1) and a polymerization initiator, polymerizing the components according to a method of heating or photoirradiation, and thereafter grinding the resultant product. As described in WO2011/115007 and WO2013/039169, the filler may be produced according to a production method for an organic-inorganic composite filler, which includes immersing inorganic aggregated particles formed by aggregation of a spherical inorganic filler (b2) in a polymerizing monomer solvent containing a polymerizing monomer, a polymerization initiator and an organic solvent, then removing the organic solvent, and polymerizing and curing the polymerizing monomer according to a method of heating or photoirradiation, thereby producing an organic-inorganic composite filler, which has an organic resin phase that covers the surface of each inorganic primary particles of the inorganic aggregated particles formed by aggregation of inorganic primary particles and mutually bonds the inorganic primary particles to each other and in which an aggregation void is formed between the organic resin phase that covers the surface of each inorganic primary particle. As the polymerization initiator herein, the same polymerization initiator as that to be described as a polymerization initiator hereinunder can be employed with no limitation, but from the viewpoint of obtaining a cured product having a lower degree of yellowness, a thermal polymerization initiator is preferably used, and above all, one that includes a compound not having an aromatic ring in the structure thereof is more preferably used.

The average particle size of the organic-inorganic composite filler (B2) in the present invention is not specifically limited, but from the viewpoint of enhancing the mechanical strength of the resin block for dental cutting work, the size is preferably 2 to 100 μm, more preferably 5 to 50 μm, even more preferably 5 to 30 μm. The average particle size of the organic-inorganic composite filler (B2) can be measured according to a laser diffraction scattering method. Also not specifically limited, the shape of the filler includes an irregularly shaped one produced by mixing a predetermined amount of each component of a spherical inorganic filler (b2), an organic resin matrix (b1) and a polymerization initiator, then polymerizing the component according to a method of heating or photoirradiation and grinding the resultant product, and a spherical or nearly spherical one produced according to the method described in WO2011/115007 or WO2013/039169.

The organic-inorganic composite filler (B2) may contain any known additive within a range not detracting from the advantageous effect thereof. Specifically, the additive includes a pigment, a polymerization inhibitor, and a fluorescent brightener. In general, these additives may be used in a ratio of generally 0.0001 to 5 parts by mass relative to 100 parts by mass of the organic-inorganic composite filler.

The organic-inorganic composite filler (B2) may be washed or surface-treated with a silane coupling agent.

The blending amount of the organic-inorganic composite filler (B2) in the present invention is, in the case where as the spherical filler (B), a powdery spherical filler (B1) is not used and the organic-inorganic composite filler (B2) alone is used, 50 to 1000 parts by mass relative to 100 parts by mass of the resin matrix (A), and for the purpose of bettering the mechanical strength of the resin block for dental cutting work, the organic-inorganic composite filler (B2) may be blended preferably in an amount of 70 to 800 parts by mass, more preferably 100 to 600 parts by mass. The blending amount of the spherical inorganic filler (b2) in the organic-inorganic composite filler is, as so described hereinabove, preferably 30% by mass or more and 95% by mass or less, more preferably 40 to 90% by mass. Accordingly, the blending amount of the spherical inorganic filler (b2) that facilitates colored light expression by interference is 10% by mass ((50/150)×30%) or more and 86.4% by mass ((1000/1100)×95%) or less. In the case where the spherical filler (B1) that is used as a powder and the organic-inorganic composite filler (B2) are used together, the two may be so combined that the total blending amount of the spherical filler (B1) and the spherical inorganic filler (b2) in the organic-inorganic composite filler (B2) could be 10 to 86% by mass in the resin block for dental cutting work, for better colored light expression by interference. The total blending amount of the spherical filler (B1) and the spherical inorganic filler (b2) in the organic-inorganic composite filler (B2) is more preferably 15% by mass to 86% by mass in the resin block for dental cutting work, even more preferably 20% by mass to 86% by mass. For further bettering the mechanical strength of the resin block for dental cutting work, the blending ratio (by mass) of the spherical filler (B1) and the organic-inorganic composite filler (B2) is preferably 90/10 to 10/90, more preferably 80/20 to 20/80, even more preferably 70/30 to 30/70.

Specifically, the blending amount of the spherical filler (B) in the resin block for dental cutting work is preferably 10 to 86% by mass, more preferably 15 to 86% by mass, even more preferably 20 to 86% by mass. Here, the blending amount of the spherical filler (B) means, when a powdery spherical filler (B1) is used as a spherical filler (B), the blending amount of the powdery spherical filler (B1), means, when the spherical filler (B) is used as an organic-inorganic composite filler (B2), the blending amount of the spherical inorganic filler (b2) in the organic-inorganic composite filler (B2), and means, when a powdery spherical filler (B1) and an organic-inorganic composite filler (B2) are used tougher, the total amount of the spherical filler (B1) and the spherical inorganic filler (b2) in the organic-inorganic composite filler (B2).

<Inorganic Particles (C)>

In the resin block for dental cutting work of the present invention, inorganic particles (C) having an average primary particle size of less than 100 nm may be further blended in addition to the spherical filler (B) whose average primary particle size falls within a range of 230 to 1000 nm, for the purpose of effectively expressing the colored light of a cured product by interference to further better the color tone compatibility thereof.

The inorganic particles (C) have an average primary particle size of less than 100 nm that hardly causes an interference phenomenon of visual light as described above, and therefore do not inhibit colored light expression by interference in the present invention. Accordingly, by incorporating the inorganic particles (C) therein, the transparency of the resin block for dental cutting work can be controlled in accordance with the blending amount of the inorganic particles (C) while securing expression of a desired colored light.

The average primary particle size of the inorganic particles (C) in the present invention is preferably 1 to 99 nm, more preferably 10 to 90 nm, even more preferably 10 to 70 nm.

As the inorganic particles (C), those usable as the spherical filler (B) in the present invention can be used with no limitation. Specifically, as the particles, inorganic powders of amorphous silica, silica-titanium group element oxide-based composite oxide particles (e.g., silica-zirconia, silica-titania), quartz, alumina, barium glass, strontium glass, lanthanum glass, fluoroaluminosilicate glass, ytterbium fluoride, zirconia, titania, or colloidal silica are usable.

Among these, amorphous silica and silica-titanium group element oxide-based composite oxide particles are preferred since the refractivity of the filler can be readily controlled.

These silica-titanium group element oxide-based composite oxide particles may be surface-treated with a silane coupling agent, like the spherical filler (B). By surface treatment with a silane coupling agent, the interface strength to the resin matrix (A) in the resin block for dental cutting work of the present invention can be bettered. Examples of a typical silane coupling agent include an organic silicon compound such as γ-methacryloyloxyalkyltrimethoxysilane, and hexamethyldisilazane. The surface treatment amount with the silane coupling agent is not specifically limited, and an optimum value thereof may be determined by previously confirming the mechanical properties of the resultant resin block for dental cutting work by experiments. An example of the preferred range of the agent is 0.1 to 15 parts by mass relative to 100 part by mass of the inorganic particles (C).

The blending amount of the inorganic particles (C) in the present invention is, from the viewpoint of color tone compatibility with natural teeth, preferably 0.1 to 50 parts by mass relative to 100 parts by mass of the resin matrix (A), more preferably 0.2 to 30 parts by mass, even more preferably 1 to 20 parts by mass.

As one typical method for dental restoration, for example, known is a method of filling a paste-like curable composition containing a (meth)acrylate-based polymerizing monomer and inorganic particles into a cavity and curing it therein. However, when a relatively large amount of the inorganic particles (C) having a small average particle size like those used in the present invention is blended in such a paste-like curable composition, the viscosity of the resultant composition increases to worsen the workability thereof. However, in the present invention, not a paste-like composition but a previously cured block is used, and therefore the workability thereof does not worsen. Accordingly, the block of the present invention containing the inorganic particles (C) blended therein secures good workability in dental restoration, and as mentioned above, the color tone compatibility thereof to natural teeth is good.

In addition, since the block is free from the risk of worsening workability mentioned above, a relatively large amount of the inorganic particles (C) can be blended therein, and accordingly, the amount of the resin component can be small to readily prevent cracking in polymerization in block production.

<Other Additives>

Any other known additive than the above-mentioned components (A) to (C) can be blended in the resin block for dental cutting work of the present invention within a range not detracting from the advantageous effects of the resin block. Specifically, a polymerization inhibitor and a UV absorbent can be blended therein.

In the present invention, as described above, there can be provided a resin block for dental cutting work that enables good restoration with a single layer of the block and has a good color tone compatibility with natural teeth even though a coloring substance such as a pigment is not used. Accordingly, an embodiment of not blending a pigment that has a risk of discoloration with time is preferred. However, in the present invention, blending of a pigment itself is not denied, and a pigment may be blended in such a degree that does not interfere with formation of colored light by interference from the spherical filler. Specifically, a pigment may be blended in an amount of 0.0005 to 0.5 parts by mass or so relative to 100 parts by mass of the resin matrix (A), preferably 0.001 to 0.3 parts by mass or so.

(Production Method for Resin Block for Dental Cutting Work)

A method for producing the resin block for dental cutting work of the present invention is not specifically limited, and an appropriate production method can be creatively used in accordance with the materials to be used. For example, in the case where the resin matrix (A) is a thermoplastic resin, employable is a method of heating and melting a kneaded mixture that contains the resin matrix (A) and a spherical filler (B) (optionally any other component such as the above-mentioned inorganic particles (C) may be added thereto), then sequentially injecting the resultant melt into the inside of a mold and molding it therein, or a method of sequentially pressing the melt inside a mold in the same manner. The spherical filler (B) to be contained in the kneaded mixture may be a powdery spherical filler (B1), or may be in the form of an organic-inorganic composite filler (B2), or may be a combination of a spherical filler (B1) and an organic-inorganic composite filler (B2).

By preparing a curable composition containing a polymerizing monomer to be a raw material for the resin matrix (A), a spherical filler (B) and a polymerization initiator (and optionally any other component such as the above-mentioned inorganic particles (C) may be added thereto), and polymerizing and curing it, a resin block for dental cutting work can also be produced.

The spherical filler (B) to be contained in the curable composition may be a powdery spherical filler (B1), or may be in the form of an organic-inorganic composite filler (B2), or may be a combination of a spherical filler (B1) and an organic-inorganic composite filler (B2). In this case, in the production process, the materials are metered, filled, shaped and defoamed inside a mold, and optionally prepolymerized by heat or light therein, and thereafter finally polymerized by heat or light to produce a block. Also if desired, the resultant block may be further treated by polishing or heat treatment.

<Polymerizing Monomer>

In the case where a curable composition containing a polymerizing monomer to be a raw material for the resin matrix (A), a spherical filler (B) and a polymerization initiator is polymerized and cured to produce a resin block for dental cutting work, the polymerizing monomer to be a raw material for the resin matrix is not specifically limited so far as it satisfies, relative to the spherical filler (B), a requirement (X2) expressed by the following expression (2)

$$nPm<nF \quad (2)$$

wherein nPm represents a refractive index at 25° C. of a polymer obtained through polymerization of the polymerizing monomer, and nF represents a refractive index of the spherical filler (B) at 25° C., and includes a radical-polymerizing monomer, and a cationic polymerizing monomer such as an epoxy compound, and an oxetane compound. As the radical polymerizing monomer, a (meth)acrylate monomer is preferably used in view of good polymerizability thereof. Examples of the (meth)acrylate polymerizing monomer include the following (a) to (c).

(a) Difunctional polymerizing monomer:
(i) Aromatic compound-type monomer:
2,2-bis(methacryloyloxyphenyl)propane,
2,2-bis[(3-methacryloyloxy-2-hydroxypropyloxy)phenyl]propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2-(4-methacyrloyloxydiethoxyphenyl)-2-(4-methacryloyloxytriethoxyphenyl)-propane,
2-(4-methacryloyloxydipropoxyphenyl)-2-(4-methacryloyloxytriethoxyphenyl)-propane,
2,2-bis(4-methacryloyloxypropoxyphenyl)propane,
2,2-bis(4-methacryloyloxyisopropoxyphenyl)propane,
and acrylates corresponding to these methacrylates;
and diadducts obtained from an adduct of a vinyl monomer having an —OH group such as a methacrylate such as
2-hydroxyethyl methacrylate,
2-hydroxypropyl methacrylate, and
3-chloro-2-hydroxypropyl methacrylate, or an acrylate corresponding to the methacrylate, and a diisocyanate compound having an aromatic group such as a diisocyanate methylbenzene, and 4,4'-diphenylmethane diisocyanate.
(ii) Aliphatic compound-type monomer:
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate,
and acrylates corresponding to these methacrylates;
diadducts obtained from an adduct of a vinyl monomer having an —OH group such as a methacrylate such as
2-hydroxyethyl methacrylate,
2-hydroxypropyl methacrylate, and
3-chloro-2-hydroxypropyl methacrylate, or acrylates corresponding to these methacrylates, and a diisocyanate compound such as
hexamethylene diisocyanate,
trimethylhexamethylene diisocyanate,
diisocyanate methylcyclohexane, isophorone diisocyanate, methylenebis(4-cyclohexyl isocyanate);
1,2-bis(3-methacryloyloxy-2-hydroxypropyl)ethyl,
1,6-bis(methacrylethyloxycarbonylamino)trimethylhexane.
(b) Trifunctional polymerizing monomer:
methacrylates such as trimethylolpropane trimethacrylate,
trimethylolethane trimethacrylate,
pentaerythritol trimethacrylate,
trimethylolmethane trimethacrylate,
and acrylates corresponding to these methacrylates.
(c) Tetrafunctional polymerizing monomer:
pentaerythritol tetramethacrylate,
pentaerythritol tetraacrylate; and
diadducts obtained from an adduct of a diisocyanate compound such as
diisocyanate methylbenzene,
diisocyanate methylcyclohexane,
isophorone diisocyanate,
hexamethylene diisocyanate,
trimethylhexamethylene diisocyanate,
methylenebis(4-cyclohexyl isocyanate),
4,4-diphenylmethane diisocyanate,
tolylene-2,4-diisocyanate, and glycidol dimethacrylate.

As needed, plural kinds of these polyfunctional (meth)arylate-type polymerizing monomers may be used in combination.

Further as needed, any other polymerizing monomer than the above-mentioned (meth)acrylate-type monomer may also be used.

In the present invention, regarding the polymerizing monomer to be a raw material for the resin matrix (A), in general, plural kinds of polymerizing monomers are used for controlling the properties (mechanical properties and for dental use, adhesiveness to teeth) of the resin block for dental cutting work, and in that case, preferably, the kind and the amount of the polymerizing monomer are determined so that the refractive index at 25° C. of the resin matrix (A) could fall within a range of 1.38 to 1.55 from the viewpoint of the refractive index difference between the resin matrix and the spherical filler (B). Specifically, in the case where a silica-titanium group element oxide-based composite oxide whose refractive index is easy to control is used as the spherical filler (B), the refractive index nF thereof may fall within a range of approximately 1.45 to 1.58 depending on the content of the silica fraction therein, and in that case, when the refractive index of the polymerizing monomer to be a raw material for the resin matrix (A) is controlled to fall within a range of 1.38 to 1.55, then the refractive index nP of the resin matrix (A) can be made to fall within a range of approximately 1.40 to 1.57 to readily satisfy the expression (1). As the case may be, plural kinds of polymerizing monomers are used for the resin matrix (A), and the refractive index of the resin material (A) in this case is a refractive index of a cured mixture of those plural kinds of polymerizing monomers, and it is good that the refractive index falls within the above-mentioned range, that is, it is not always necessary that the refractive index of each cured polymerizing monomer falls within the range.

The refractive index of the resin matrix (A) and the polymerizing monomer can be measured at 25° C. using an Abbe's refractometer.

<Polymerization Initiator>

In the case where a polymerizing monomer is used as a raw material for the resin matrix (A), preferably, a polymerization initiator is used for polymerizing and curing the polymerizing monomer. As a method for polymerizing the curable composition, any method of reaction with light energy such as UV ray or visible ray (hereinafter referred to as photopolymerization), or chemical reaction with a peroxide and an accelerator, or reaction with thermal energy (hereinafter referred to as thermal polymerization) is employable here. From the viewpoint that the timing for polymerization can be arbitrarily selected in accordance with external energy such as light or heat and that the process of operation is simple, photopolymerization or thermal polymerization is preferred. Various polymerization initiators mentioned below may be appropriately selected and used depending on the polymerization method to be employed.

Examples of usable photopolymerization initiators include benzoin alkyl ethers such as benzoin methyl ether, benzoin ethyl ether, and benzoin isopropyl ether; benzyl ketals such as benzyl dimethyl ketal, and benzyl diethyl ketal; benzophenones such as benzophenone, 4,4'-dimethylbenzophenone, and 4-methacryloxybenzophenone; α-diketones such as diacetyl, 2,3-pentadione benzyl, camphor quinone, 9,10-phenantharaquinone, and 9,10-anthraquinone; thioxanthone compounds such as 2,4-diethoxythioxanthone, 2-chlorothioxanthone, and methylthioxanthone; and acylphosphine oxides such as bis(2,6-dichlorobenzoyl) phenylphosphine oxide, bis(2,6-dichlorobenzoyl)-2,5-dimethylphenylphosphine oxide, bis(2,6-dichlorobenzoyl)-4-propylphenylphosphine oxide, bis-(2,6-dichlorobenzoyl)-1-naphthylphosphine oxide, 2,4,6-trimethylbenzoyl-diphenylphosphine oxide, and bis(2,4,6-trimethylbenzoyl)-phenylphosphine oxide.

A reducing agent is often added to the photopolymerization initiator, and examples thereof include tertiary amines such as 2-(dimethylamino)ethyl methacrylate, ethyl 4-dimethylaminobenzoate, and N-methyldiethanolamine; aldehydes such as lauryl aldehyde, dimethylaminobenzaldehyde, and terephthalaldehyde; and sulfur-containing compounds such as 2-mercaptobenzoxazole, 1-decanethiol, thiosalicylic acid, and thiobenzoic acid.

Examples of thermal polymerization initiators include peroxides such as benzoyl peroxide, p-chlorobenzoyl peroxide, tert-butylperoxy-2-ethyl hexanoate, tert-butylperoxy dicarbonate, and diisopropylperoxy dicarbonate; azo compounds such as azobisisobutyronitrile; boron compounds such as tributyl borane, tributyl borane partial oxide, sodium tetraphenylborate, sodium tetrakis(p-fluorophenyl)borate, and tetraphenylboric acid triethanolamine salt; barbituric acids such as 5-butylbarbituric acid, and 1-benzyl-5-phenyl-barbituric acid; sulfinates such as sodium benzenesulfinate, and sodium p-toluenesulfinate.

One alone or two or more kinds of these polymerization initiators may be used either singly or as combined. The blending amount of the polymerization initiator is preferably 0.01 to 5 parts by mass relative to 100 parts by mass of the polymerizing monomer.

(Method of Using Resin Block for Dental Cutting Work)

The block produced in the manner as above is, optionally after a pin for holding the block on a CAD/CAM device is bonded thereto, usable as a CAD/CAM block. This may be connected to a CAD/CAM device and cut as designed to give a dental prosthesis such as an inlay, an onlay, a crown, a bridge or an implant upper structure.

The resin block for dental cutting work of the present invention is applicable to restoration of a cavity of any size, and is favorably applicable to restoration of even a large cavity. Consequently, the resin block for dental cutting work of the present invention is favorably used as a dental prosthesis such as the above-mentioned inlay, onlay, crown, bridge and implant upper structure.

EXAMPLES

Hereinunder the present invention is described more specifically with reference to Examples, but the present invention is not whatsoever restricted by these Examples.

Methods for measuring various properties in the present invention are as mentioned below.

(1) Average Primary Particle Size of Spherical Filler (B) and Inorganic Particles (C)

Using a scanning electron microscope (from Philips N.V., "XL-30S"), a picture of the powder to be analyzed was taken at 5000- to 100000-fold magnification, and using image analyzing software ("IP-1000PC", product name; from Asahi Kasei Engineering Corporation), the picture was manipulated, and the number of the particles (30 or more particles) seen in the unit field of view of the picture was counted and the primary particle size (maximum diameter) thereof was measured. From the measured data, the number average primary particle size was calculated according to the following equation.

$$\bar{x} = \frac{\sum_{i=1}^{n} x_i}{n} \text{ (number average)}$$

(n: number of particles, $x_i$: primary particle size (maximum diameter) of i'th particle)

(2) Proportion of Particles Falling in a Range of Average Particle Size in Spherical Filler (B)

A proportion (%) of particles falling within a range of average primary particle size±5% in the spherical filler (B) was calculated as follows. Among all the particles (30 particles or more) in the unit field of view of the picture, the number of the particles having a primary particle size (maximum diameter) not falling within a range of average primary particle size±5% as calculated in the above was counted, and the count was subtracted from the number of all the particles to give the number of the particles falling within a range of average primary particle size±5% in the unit field of view of the picture, and the proportion (%) of the particles falling within a range of average primary particle size±5% in the spherical filler (B) was calculated according to the following equation.

Proportion (%) of particles falling within a range of average primary particle size±5% in spherical filler (B)=[(number of particles falling within a range of average primary particle size±5% in the unit field of view of scanning electron microscopic picture)/(number of all particles in the unit field of view of scanning electron microscopic picture)]×100

(3) Average Evenness of Spherical Filler (B)

Using a scanning electron microscope, a picture of the powder to be analyzed was taken, and on the picture, the number (n: 30 or more) of the particles seen in the unit field of view, and the maximum diameter of the particles as a major diameter (Li) and the diameter thereof in the direction perpendicular to the major diameter as a minor diameter (Bi) were measured, and the average evenness of the spherical filler (B) was calculated according to the following equation.

$$\text{Average evenness} = \frac{\sum_{i=1}^{n} Bi/Li}{n}$$

(4) Average Particle Size (Granularity) of Organic-Inorganic Composite Filler 0.1 g of an organic-inorganic composite filler was dispersed in 10 ml of ethanol and irradiated with ultrasonic waves for 20 minutes. Using a particle size analyzer ("LS230", from Beckman Coulter Inc.) according to a laser diffraction-scattering method, and applying an optical model "Fraunhofer" thereto, a median diameter in volume statistics of the filler was determined.

(5) Measurement of Refractive Index

<Refractive Index (nP) of Resin Matrix (A)>

The refractive index of the resin matrix (A) used is a refractive index of the polymer produced through polymerization of the polymerizing monomer of a raw material for the resin matrix (A). Specifically, a polymer produced through polymerization under the same condition as that for production of a block for dental cutting work was measured in a temperature-controlled room at 25° C. using an Abbe's refractometer (from Atago Co., Ltd.).

Specifically, a uniform mixture of a polymerizing monomer mixed with 0.5% by mass of BPO was put into a mold having a through-hole of 7 mmφ×0.5 mm, and a polyester film was stuck under pressure to both surfaces thereof. Subsequently, this was polymerized and cured by heating under nitrogen pressure for 1 hour, and then taken out of the mold to give a resin matrix (A). In setting the resin matrix to an Abbe's refractometer (from Atago Co., Ltd.), the sample was not melted and a solvent (bromonaphthalene) having a higher refractive index than that of the sample was dropwise added to the sample for measurement, for the purpose of airtightly attaching the matrix and the measurement surface.

<Refractive Index $nM_{b1}$ of Organic Resin Matrix (b1)>

The refractive index of the organic resin matrix (b1) is a refractive index of the polymer produced through polymerization of the polymerizing monomer of a raw material for the organic resin matrix (b1). Specifically, a polymer produced through polymerization under substantially the same condition as that for production of an organic-inorganic composite filler was measured in a temperature-controlled room at 25° C. using an Abbe's refractometer (from Atago Co., Ltd.).

Specifically, a uniform polymerizing monomer (or a uniform mixture of a polymerizing monomer) mixed with 0.5% by mass of AIBN was put into a mold having a through-hole of 7 mmφ×0.5 mm, and a polyester film was stuck under pressure to both surfaces thereof. Subsequently, this was polymerized and cured by heating under nitrogen pressure for 1 hour, and then taken out of the mold to give an organic resin matrix (b1). In setting the organic resin matrix to an Abbe's refractometer (from Atago Co., Ltd.), the sample was not melted and a solvent (bromonaphthalene) having a higher refractive index than that of the sample was dropwise added to the sample for measurement, for the purpose of airtightly attaching the matrix and the measurement surface.

<Refractive Index of Spherical Filler (B) and Inorganic Particles (C)>

The refractive index of the spherical filler (B) and the inorganic particles (C) used was measured according to an immersion method, using an Abbe's refractometer (from Atago Co., Ltd.).

Specifically, in a temperature-controlled room at 25° C., 1 g of a spherical filler (B), or inorganic particles (C) or a surface-treated sample thereof was dispersed in 50 ml of anhydrous toluene in a 100-ml sample bottle. While the resultant dispersion was stirred with a stirrer, 1-bromotoluene was dropwise and little by little added thereto, and the refractive index of the dispersion at the time at which the dispersion became most transparent was measured, and the thus-measured value is referred to as the refractive index of the inorganic filler.

(6) Visual Evaluation of Colored Light

A cured sample having a length of 7 mm, a width of 7 mm and a thickness of 1 mm was cut out of the resin block for dental cutting work prepared in Examples and Comparative Examples, and put on the adhesive surface of a black adhesive tape (carbon tape) having a size of around 10 mm square in such a manner that the thickness direction of the cured sample could be vertical to the adhesive surface, and the color tone of the colored light of the sample was visually checked.

(7) Wavelength of Colored Light

A cured sample having a length of 7 mm, a width of 7 mm and a thickness of 1 mm was cut out of the resin block for dental cutting work prepared in Examples and Comparative Examples, and using a colorimeter (from Tokyo Denshoku Co., Ltd., "TC-1800MKII"), the spectral reflectivity of the sample was measured on a black background (a base with a lightness of 1 according to the Munsell color system) and on a white background (a base with a lightness of 9.5 according to the Munsell color system), and the maximum point of the reflectivity on a black background is referred to as the wavelength of the colored light. The cured sample was put in such a manner that the thickness direction thereof could be vertical to the surface of the base.

(8) Hue, Lightness, Saturation

In the same manner as above, cured samples each having a thickness of 1 mm or 10 mm were cut out of the resin block for dental cutting work. Using a colorimeter (from Tokyo Denshoku Co., Ltd., "TC-1800MKII"), the hue (H), the lightness (V) and the saturation (C) according to the Munsell color system of each cured sample having a different thickness were measured on a black background (a base with a lightness of 1 according to the Munsell color system) and on a white background (a base with a lightness of 9.5 according to the Munsell color system), according to JIS Z8722. Also in the same manner as above, the cured sample was put in such a manner that the thickness direction thereof could be vertical to the surface of the base.

(9) Evaluation of Color Tone Compatibility

For evaluation of color tone compatibility, a model tooth for restoration (hard resin tooth) composed of a dentin part and an enamel part and in which the dentin part was covered with the enamel part was used. Specifically, the resin block for dental cutting work prepared in Examples and Comparative Examples was cut to produce a dental prosthesis (for restoration) in order that the thus-produced prosthesis could be compatible with the lost part of a model tooth for tooth restoration that was to reproduce a II class cavity (diameter: 5 mm, depth: 3 mm) in the lower right number 6 (lateral diameter 10 mm: abutment/cavity forming model tooth [A55AN-465] right lower jaw 6, second-class MOD cavity, from NISSIN Corporation), and then using Estecem II (adhesive resin cement, from Tokuyama Dental Corporation), this was bonded and polished to visually confirm the color tone compatibility thereof. As the model tooth for tooth restoration, herein used were a high-saturation high-chromaticity model tooth (corresponding to A4) and a low-saturation low-chromaticity model tooth (corresponding to A1) falling within a range of A category (red-brown) in a shade guide "VITAPAN Classical (registered trademark)", and a high-saturation high-chromaticity model tooth (corresponding to B4) and a low-saturation low-chromaticity model tooth (corresponding to B1) falling within a range of B category (red-yellow) in the shade guide "VITAPAN Classical (registered trademark)".

Color Tone Compatibility Evaluation Criteria:

A: The color tone of the restoration is well compatible with the model tooth for tooth restoration.

Depending on the degree of compatibility, the samples were evaluated in more detail in two grades of A1>A2.

The evaluation means that A1 is more excellent in color tone compatibility than A2.

B: The color tone of the restoration is similar to that of the model tooth for tooth restoration.

Depending on the degree of similarity, the samples were evaluated in more detail in two grades of B1>B2.

The evaluation means that B1 is more excellent in color tone compatibility than B2.

C: The color tone of the restoration is similar to that of the model tooth for tooth restoration but the compatibility thereof is not good.

D: The color tone of the restoration is not compatible with that of the model tooth for tooth restoration.

(10) Color Tone Change with Time

A cured sample of 7 mmφ×1 mm was cut out of the resin block for dental cutting work prepared in Examples and Comparative Examples, and stored in water at 37° C. for 4 months. Then, using a colorimeter (from Tokyo Denshoku Co., Ltd., "TC-1800MKII"), the color tone of each sample was measured, and the color tone difference before and after storage was expressed as ΔE* in CIE Lab.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

wherein L1* represents a lightness index of the cured sample after storage; a1* and b1* represent color quality index after storage; L2* represents a lightness index of the cured sample before storage; a2* and b2* represent color quality index before storage; and ΔE* represents amount of color tone change.

(11) Evaluation of Bending Strength

A test piece having a width of 2 mm and a length of 25 mm was cut out of the resin block for dental cutting work prepared in Examples and Comparative Examples, and polished with waterproof sandpaper No. 1500 in the lengthwise direction of the thus-cut test piece to be a test piece having a thickness of 2±0.1 mm.

Using a universal tensile tester autograph (from Shimadzu Corporation), the test piece was tested in a 3-point bending test under the condition of an inter-fulcrum distance of 20 mm and a cross head speed of 1 mm/min, at room temperature in air. Five test pieces were tested to measure the bending strength thereof, and the data were averaged to give an average value of the bending strength of the test pieces.

The polymerizing monomer, the polymerization initiator and the organic particles used in Examples and Comparative Examples are as follows.

[Polymerizing Monomer]
1,6-Bis(methacrylethyloxycarbonylamino)trimethylhexane (hereinunder abbreviated as "UDMA")
Triethylene glycol dimethacrylate (hereinunder abbreviated as "3G")
2,2-Bis[(3-methacryloyloxy-2-hydroxypropyloxy)phenyl] propane (hereinunder abbreviated as "bis-GMA")

[Polymerization Initiator]
Benzoyl peroxide (hereinunder abbreviated as "BPO")
Azobisisobutyronitrile (hereinunder abbreviated as "AIBN")

[Inorganic Particles (C)]
Reoroseal QS-102 (average primary particle size 12 nm, from Tokuyama Corporation)

[Colorant]
Titanium dioxide (white pigment)
Pigment yellow (yellow pigment)
Pigment red (red pigment)
Pigment blue (blue pigment)

As shown in Table 1, polymerizing monomers were mixed to prepare matrixes M1, M2 and M3.

TABLE 1

| Monomer | Polymerizing Monomer Components | Refractive Index | |
| --- | --- | --- | --- |
| | | before curing | after curing |
| M1 | UDMA(60)/3G(40) | 1.474 | 1.509 |
| M2 | bis-GMA(50)/3G(50) | 1.506 | 1.540 |
| M3 | bis-GMA(30)/3G(70) | 1.488 | 1.528 |

In Table 1, the parenthesized value means part by mass.

[Production of Spherical Filler and Irregularly Shaped Filler]

A spherical filler was produced according to the method described in JP 58-110414 A or JP 58-156524 A, in which a precipitate of a reaction product is prepared according to a so-called sol-gel process of adding a mixed solution that contains a hydrolyzable organic silicon compound (e.g., tetraethyl silicate) and a hydrolyzable organic titanium group metal compound (e.g., tetrabutyl zirconate or tetrabutyl titanate) to an ammonia-containing alcohol (e.g., methanol, ethanol, isopropyl alcohol or isobutyl alcohol) to which aqueous ammonia has been introduced followed by hydrolyzing the solution to give a reaction product precipitate, and then the precipitate is dried and optionally ground and fired.

An irregularly shaped filler was produced according to the method described in JP 2-132102 A or JP 3-197311 A, in which an alkoxysilane compound is dissolved in an organic solvent, then water is added thereto for partially hydrolyzing the compound, and further an alkoxide of any other metal or an alkali metal compound for complex formation is added to hydrolyze the compound to form a gel product, and then the gel product is dried and optionally ground and fired.

The spherical filler (B) and the irregularly shaped filler used in Examples are silica-zirconia of silica-titanium group element oxide-based composite oxide particles, and the details thereof are shown in Table 2.

The spherical filler (B) shown in Table 2 was used as a raw material (spherical inorganic filler (b2)) for producing the organic-inorganic composite filler (B2) or as the powdery spherical filler (B1) to be blended in Examples.

[Production of Nearly Spherical Organic-Inorganic Composite Filler]

200 g of water was added to 100 g of the spherical inorganic filler shown in Table 2 and processed using a circulation-type grinding machine SC mill (from Nippon Coke & Engineering Co., Ltd.) to give an aqueous dispersion (spherical inorganic filler dispersion).

On the other hand, 4 g (0.016 mol) of γ-methacryloyloxypropyl-trimethoxysilane and 0.003 g of acetic acid were added to 80 g of water, and stirred for 1 hour and 30 minutes to prepare a uniform solution having a pH of 4. The solution was added to the above-mentioned spherical inorganic filler dispersion and mixed to be uniform. Subsequently, while lightly mixed, the dispersion was applied onto a disc rotating at a high speed and granulated according to a spray drying method.

Spray drying was carried out using a spray drier TSR-2W (from Sakamoto Giken Co., Ltd.) equipped with a rotary disc for centrifugal atomization. The rotating speed of the disc was 10000 rpm, and the temperature of the dry atmosphere air was 200° C. Subsequently, the powder thus

TABLE 2

| | Composition and Shape of Filler | | Average Particle | Refractive | Proportion (%) of Particles falling within a range of average particle | Average |
|---|---|---|---|---|---|---|
| | Composition (mol %) | Shape | Size (nm) | Index | size (%)* | Evenness |
| PF1 | $SiO_2/ZrO_2/Na_2O$ = 89.8/9.0/1.2 | spherical | 178 | 1.515 | 91 | 0.98 |
| PF2 | $SiO_2/ZrO_2/Na_2O$ = 89.8/9.0/1.2 | spherical | 230 | 1.515 | 92 | 0.97 |
| PF3 | $SiO_2/ZrO_2/Na_2O$ = 89.8/9.0/1.2 | spherical | 303 | 1.515 | 90 | 0.92 |
| PF4 | $SiO_2/ZrO_2/Na_2O$ = 89.8/9.0/1.2 | spherical | 80 | 1.515 | 92 | 0.94 |
| PF5 | $SiO_2/ZrO_2/Na_2O$ = 89.8/9.0/1.2 | spherical | 280 | 1.515 | 94 | 0.94 |
| PF6 | $SiO_2/ZrO_2/Na_2O$ = 88.7/10.1/1.2 | spherical | 282 | 1.522 | 93 | 0.92 |
| PF7 | $SiO_2/ZrO_2/Na_2O$ = 83.9/14.3/1.8 | spherical | 286 | 1.542 | 91 | 0.90 |
| PF8 | $SiO_2/ZrO_2/Na_2O$ = 90.1/8.7/1.2 | spherical | 280 | 1.522 | 95 | 0.95 |
| PF9 | $SiO_2/ZrO_2/Na_2O$ = 88.7/10.1/1.2 | spherical | 340 | 1.522 | 88 | 0.93 |
| PF10 | $SiO_2/ZrO_2/Na_2O$ = 88.7/10.1/1.2 | spherical | 260 | 1.522 | 93 | 0.94 |
| PF11 | $SiO_2/ZrO_2/Na_2O$ = 89.8/9.0/1.2 | irregularly shaped | 500 | 1.515 | 50 | — |

*Proportion of particles falling within a range of average particle size means a proportion of particles falling within a range of average particle size ± 5%.

[Production of Irregularly Shaped Organic-Inorganic Composite Filler]

The thermal polymerization initiator (AIBN) was previously dissolved in a ratio by mass of 0.5% in the matrix shown in Table 1, and a predetermined amount (Table 3) of the spherical inorganic filler or the irregularly shaped inorganic filler shown in Table 2 was added thereto and mixed in a mortar to prepare a paste. This was polymerized and cured by heating under nitrogen pressure at 95° C. for 1 hour. The cured product was ground with a vibration ball mill, and further surface-treated with 0.02% by mass of γ-methacryloyloxypropyltrimethoxysilane by refluxing in ethanol at 90° C. for 5 hours to give irregularly shaped organic-inorganic composite fillers CF1 to CF13 as shown in Table 3.

produced by spray drying granulation was dried in vacuum at 60° C. for 18 hours to give 73 g of a nearly spherical aggregate.

Next, the thermal polymerization initiator AIBN was added in a ratio by mass of 0.5% to the matrix shown in Table 1, and further a predetermined amount (Table 3) of the above-mentioned aggregate was added to the polymerizing monomer solution mixed with an organic solvent of methanol (containing 36 parts by mass of the polymerizing monomer relative to 100 parts by mass of the organic solvent) and impregnated therein. After confirmed to be a slurry by fully stirring, the resultant mixture was kept statically for 1 hour.

The mixture was transferred to a rotary evaporator. While kept stirred, the mixture was dried under a condition of a reduced pressure of 10 hPa and a heating condition of 40° C.

(using a hot water bath) for 1 hour to remove the organic solvent. After the organic solvent was removed, a powder of high fluidity was obtained.

With stirring in a rotary evaporator, the resultant powder was heated for 1 hour under a condition of a reduced pressure of 10 hPa and a heating condition of 100° C. (using an oil bath) to thereby polymerize and cure the polymerizing monomer in the powder. As a result of drying, the surface of the spherical inorganic filler aggregate was coated with an organic polymer and nearly spherical organic-inorganic composite fillers CF14 to CF16 shown in Table 3 below were produced each in an amount of 9 g.

TABLE 3

| | Composition and Shape of Organic-Inorganic Composite Filler | | | Filler Filling Rate (wt %) | Average Particle Size (μm) |
|---|---|---|---|---|---|
| | Matrix (b1) | Inorganic Filler (b2) | Shape | | |
| CF1 | M1(100) | PF1(300) | irregularly shaped | 75 | 30 |
| CF2 | M1(100) | PF2(300) | irregularly shaped | 75 | 28 |
| CF3 | M1(100) | PF3(300) | irregularly shaped | 75 | 31 |
| CF4 | M1(100) | PF4(300) | irregularly shaped | 75 | 24 |
| CF5 | M1(100) | PF5(300) | irregularly shaped | 75 | 29 |
| CF6 | M1(100) | PF5(233) | irregularly shaped | 70 | 28 |
| CF7 | M1(100) | PF5(150) | irregularly shaped | 60 | 33 |
| CF8 | M1(100) | PF5(400) | irregularly shaped | 80 | 31 |
| CF9 | M2(100) | PF7(300) | irregularly shaped | 75 | 32 |
| CF10 | M1(100) | PF8(300) | irregularly shaped | 75 | 29 |
| CF11 | M1(100) | PF9(300) | irregularly shaped | 75 | 30 |
| CF12 | M1(100) | PF10(300) | irregularly shaped | 75 | 34 |
| CF13 | M1(100) | PF11(300) | irregularly shaped | 75 | 28 |
| CF14 | M1(100) | PF5(300) | nearly spherical | 75 | 30 |
| CF15 | M3(100) | PF6(300) | nearly spherical | 75 | 25 |
| CF16 | M2(100) | PF7(300) | nearly spherical | 75 | 32 |

In Table 3, the parenthesized value means part by mass.

Examples 1 to 18

BPO in an amount of 0.5% by mass was added to the matrix M1 or M2 shown in Table 1 and mixed to prepare a uniform polymerizing monomer composition. Next, the filler and the inorganic particles (C) shown in Table 2 and Table 3 were weighed, and mixed with the matrix in the blending ratio as shown in Table 4, and well dispersed using a planetary mixer to prepare a curable composition. This was defoamed in vacuum and filled into a mold of 14×18 mm up to a height of 150 mm so as not to engulf foams therein, then the top face was smoothed and, using a thermal pressure polymerizing chamber, this was thermally polymerized under pressure under a condition of a pressure of 3 kgf/cm$^2$, at 120° C. for 30 minutes. A cured composition was taken out of the mold to be a resin block for dental cutting work. The properties of the resultant resin block for dental cutting work were evaluated according to the above-mentioned methods. The compositions and the results are shown in Table 4, Table 5, and Table 6.

Comparative Examples 1 to 7, and 9 to 10

BPO in an amount of 0.5% by mass was added to the matrix M1, M2 or M3 and mixed to prepare a uniform polymerizing monomer composition. Next, the filler and the inorganic particles (C) shown in Table 2 and Table 3 were weighed, and mixed with the matrix in the blending ratio as shown in Table 4, and well dispersed using a planetary mixer to prepare a curable composition. This was defoamed in vacuum and filled into a mold of 14×18 mm up to a height of 150 mm so as not to engulf foams therein, then the top face was smoothed and, using a thermal pressure polymerizing chamber, this was thermally polymerized under pressure under a condition of a pressure of 3 kgf/cm$^2$, at 120° C. for 30 minutes. A cured composition was taken out of the mold to be a resin block for dental cutting work. The properties of the resultant resin block for dental cutting work were evaluated according to the above-mentioned methods. The compositions and the results are shown in Table 4, Table 5, and Table 6.

Comparative Example 8

BPO in an amount of 0.5% by mass was added to the matrix M1 and mixed to prepare a uniform polymerizing monomer composition. Next, the filler shown in Table 2 and Table 3 was weighed, and mixed with the matrix in the blending ratio as shown in Table 4, then titanium dioxide (white pigment) in an amount of 0.04% by mass, pigment yellow (yellow pigment) in an amount of 0.1% by mass, pigment red (red pigment) in an amount of 0.09% by mass, and pigment blue (blue pigment) in an amount of 0.06% by mass were added to the composition and well dispersed using a planetary mixer to prepare a curable composition. This was defoamed in vacuum and filled into a mold of 14×18 mm up to a height of 150 mm so as not to engulf foams therein, then the top face was smoothed and, using a thermal pressure polymerizing chamber, this was thermally polymerized under pressure under a condition of a pressure of 3 kgf/cm$^2$, at 120° C. for 30 minutes. A cured composition was taken out of the mold to be a resin block for dental cutting work. In visual evaluation, the resin block was confirmed to have a color tone (corresponding to A4) compatible with the category A of a high-saturation hard resin tooth. Subsequently, the properties of the resin block were evaluated according to the above-mentioned methods. The composition and the results are shown in Table 4, Table 5, and Table 6.

TABLE 4

| | Resin Matrix (A) | Spherical Filler (B) | | Inorganic Particles (C) | Visual Evaluation of Colored Light | Colored Light Wavelength (nm) black background | Colored Light Wavelength (nm) white background | Mold Volume (cm$^3$) | Bending Strength (MPa) |
|---|---|---|---|---|---|---|---|---|---|
| | | Organic-Inorganic Composite Filler (B2) | Spherical Filler (B1) | | | | | | |
| Example 1 | M1(100) | — | PF2(500) | — | yellow | 607 | no maximum | 37.8 | 170 |
| Example 2 | M1(100) | CF2(300) | PF2(200) | — | yellow | 610 | no maximum | 37.8 | 185 |
| Example 3 | M1(100) | — | PF3(500) | 0.5 | red | 756 | no maximum | 37.8 | 171 |
| Example 4 | M1(100) | CF5(300) | PF5(200) | 0.5 | red | 757 | no maximum | 37.8 | 190 |
| Example 5 | M1(100) | CF5(500) | — | — | red | 752 | no maximum | 37.8 | 172 |

TABLE 4-continued

| | Resin Matrix (A) | Spherical Filler (B) Organic-Inorganic Composite Filler (B2) | Spherical Filler (B1) | Inorganic Particles (C) | Visual Evaluation of Colored Light | Colored Light Wavelength (nm) black background | Colored Light Wavelength (nm) white background | Mold Volume (cm$^3$) | Bending Strength (MPa) |
|---|---|---|---|---|---|---|---|---|---|
| Example 6 | M1(100) | CF6(500) | — | — | red | 750 | no maximum | 37.8 | 170 |
| Example 7 | M1(100) | CF7(500) | — | — | red | 747 | no maximum | 37.8 | 171 |
| Example 8 | M1(100) | CF8(500) | — | — | red | 755 | no maximum | 37.8 | 173 |
| Example 9 | M2(100) | CF9(300) | PF7(200) | — | red | 755 | no maximum | 37.8 | 183 |
| Example 10 | M1(100) | CF3(290) | PF3(210) | — | red | 756 | no maximum | 37.8 | 185 |
| Example 11 | M1(100) | CF10(280) | PF8(220) | — | red | 753 | no maximum | 37.8 | 198 |
| Example 12 | M1(100) | CF12(250) | PF10(250) | — | red | 688 | no maximum | 37.8 | 178 |
| Example 13 | M1(100) | CF14(500) | — | — | red | 751 | no maximum | 37.8 | 170 |
| Example 14 | M1(100) | CF14(300) | PF5(200) | — | red | 754 | no maximum | 37.8 | 203 |
| Example 15 | M1(100) | CF14(300) | PF5(200) | 0.5 | red | 752 | no maximum | 37.8 | 207 |
| Example 16 | M1(100) | CF14(300) | PF5(195) | 5 | red | 747 | no maximum | 37.8 | 205 |
| Example 17 | M2(100) | CF16(300) | PF7(200) | — | red | 753 | no maximum | 37.8 | 197 |
| Example 18 | M1(100) | CF14(500) | — | 0.5 | red | 752 | no maximum | 37.8 | 174 |
| Comparative Example 1 | M1(100) | — | PF1(500) | — | blue | 481 | no maximum | 37.8 | 170 |
| Comparative Example 2 | M1(100) | CF1(500) | — | — | blue | 479 | no maximum | 37.8 | 176 |
| Comparative Example 3 | M1(100) | CF4(300) | PF4(200) | — | no | 405 | no maximum | 37.8 | 175 |
| Comparative Example 4 | M1(100) | — | PF9(500) | 0.5 | pale red | 740 | no maximum | 37.8 | 169 |
| Comparative Example 5 | M1(100) | — | PF11(500) | 0.5 | no | no maximum | no maximum | 37.8 | 168 |
| Comparative Example 6 | M1(100) | CF11(300) | PF9(200) | 0.5 | pale red | 741 | no maximum | 37.8 | 180 |
| Comparative Example 7 | M1(100) | CF13(500) | — | — | no | no maximum | no maximum | 37.8 | 174 |
| Comparative Example 8 | M1(100) | CF4(300) | PF4(200) | — | red | no maximum | no maximum | 37.8 | 189 |
| Comparative Example 9 | M2(100) | — | PF5(500) | — | blue | 477 | no maximum | 37.8 | 170 |
| Comparative Example 10 | M3(100) | CF15(500) | — | — | blue | 475 | no maximum | 37.8 | 176 |

In Table 4, the parenthesized values for the resin matrix (A), the spherical filler (B1), and the organic-inorganic composite filler (B2), and the numerical value for the organic particles (C) are part by mass.

TABLE 5

| | Color Tone (thickness 10 mm) | | | | | | Color Tone (thickness 1 mm) | | |
|---|---|---|---|---|---|---|---|---|---|
| | on black background | | | on white background | | | on black background | | |
| | Hue (H) | Lightness (V) | Saturation (C) | Hue (H) | Lightness (V) | Saturation (C) | Hue (H) | Lightness (V) | Saturation (C) |
| Example 1 | 7.65Y | 4.82 | 0.68 | 6.17Y | 4.84 | 0.68 | 5.35Y | 3.10 | 0.50 |
| Example 2 | 7.31Y | 4.76 | 0.65 | 7.02Y | 4.73 | 0.66 | 5.80Y | 3.53 | 0.42 |
| Example 3 | 8.05Y | 4.81 | 0.51 | 7.33Y | 4.82 | 0.55 | 9.93YR | 3.17 | 0.07 |
| Example 4 | 7.02Y | 4.65 | 0.34 | 7.09Y | 4.55 | 0.31 | 6.41YR | 3.55 | 0.21 |
| Example 5 | 6.89Y | 4.52 | 0.33 | 6.97Y | 4.48 | 0.31 | 6.39YR | 3.52 | 0.22 |
| Example 6 | 6.24Y | 4.73 | 0.53 | 6.31Y | 4.67 | 0.55 | 6.40YR | 3.55 | 0.23 |
| Example 7 | 6.77Y | 4.67 | 0.48 | 6.79Y | 4.62 | 0.47 | 6.35YR | 3.50 | 0.19 |
| Example 8 | 6.43Y | 4.22 | 0.78 | 6.44Y | 4.21 | 0.79 | 6.41YR | 3.54 | 0.21 |
| Example 9 | 7.23Y | 4.18 | 0.81 | 7.00Y | 4.11 | 0.83 | 6.44YR | 3.53 | 0.25 |
| Example 10 | 5.06Y | 3.98 | 0.83 | 5.11Y | 3.87 | 0.85 | 9.88YR | 3.21 | 0.12 |
| Example 11 | 7.14Y | 4.53 | 0.37 | 7.09Y | 4.48 | 0.41 | 6.53YR | 3.61 | 0.28 |
| Example 12 | 7.09Y | 3.86 | 0.84 | 7.03Y | 3.89 | 0.85 | 1.18Y | 3.33 | 0.36 |
| Example 13 | 6.87Y | 3.77 | 0.78 | 6.88Y | 3.73 | 0.74 | 6.40YR | 3.52 | 0.24 |
| Example 14 | 6.45Y | 3.23 | 0.74 | 6.42Y | 3.33 | 0.77 | 6.38YR | 3.48 | 0.24 |
| Example 15 | 6.99Y | 4.21 | 0.43 | 7.08Y | 4.29 | 0.45 | 6.37YR | 3.51 | 0.22 |
| Example 16 | 7.11Y | 4.67 | 0.56 | 7.17Y | 4.65 | 0.58 | 6.33YR | 3.47 | 0.18 |
| Example 17 | 7.71Y | 4.32 | 0.61 | 7.73Y | 4.34 | 0.63 | 6.42YR | 3.51 | 0.23 |
| Example 18 | 6.62Y | 3.66 | 0.61 | 6.77Y | 3.75 | 0.63 | 6.37YR | 3.50 | 0.23 |
| Comparative Example 1 | 4.15B | 4.66 | 5.11 | 4.05B | 4.67 | 5.09 | 6.53B | 2.52 | 4.03 |
| Comparative Example 2 | 4.22B | 4.63 | 5.08 | 4.18B | 4.61 | 5.03 | 6.52B | 2.53 | 4.01 |

TABLE 5-continued

| | | | | | | | | |
|---|---|---|---|---|---|---|---|---|
| Comparative Example 3 | 6.56PB | 2.75 | 5.46 | 6.82PB | 2.85 | 5.16 | 5.42PB | 1.40 | 2.20 |
| Comparative Example 4 | 7.05Y | 4.89 | 0.99 | 7.07Y | 4.87 | 1.01 | 8.22YR | 5.14 | 0.04 |
| Comparative Example 5 | 4.24B | 4.77 | 5.15 | 4.23B | 4.75 | 5.06 | 6.72B | 5.78 | 0.79 |
| Comparative Example 6 | 7.12Y | 4.78 | 0.88 | 7.09Y | 4.77 | 0.84 | 8.24YR | 5.12 | 0.03 |
| Comparative Example 7 | 4.00B | 4.78 | 5.23 | 4.02B | 4.77 | 5.21 | 6.67B | 5.79 | 0.77 |
| Comparative Example 8 | 4.12Y | 4.85 | 1.19 | 4.04Y | 4.83 | 1.17 | 5.38B | 4.13 | 0.69 |
| Comparative Example 9 | 4.16B | 4.88 | 5.01 | 4.17B | 4.86 | 5.07 | 5.68B | 4.56 | 0.68 |
| Comparative Example 10 | 4.17B | 4.85 | 5.03 | 4.15B | 4.86 | 5.04 | 5.71B | 4.58 | 0.72 |

| | Color Tone (thickness 1 mm) on white background | | | |
|---|---|---|---|---|
| | Hue (H) | Lightness (V) | Saturation (C) | Color Tone Change with Time ΔE* |
| Example 1 | 2.15Y | 7.52 | 1.05 | 2.0 |
| Example 2 | 2.12Y | 7.47 | 1.01 | 2.2 |
| Example 3 | 1.31Y | 7.23 | 0.98 | 1.4 |
| Example 4 | 1.31Y | 7.25 | 0.97 | 1.4 |
| Example 5 | 1.33Y | 7.21 | 0.98 | 1.3 |
| Example 6 | 1.35Y | 7.24 | 0.99 | 1.5 |
| Example 7 | 1.36Y | 7.25 | 0.98 | 1.4 |
| Example 8 | 1.33Y | 7.22 | 0.97 | 1.4 |
| Example 9 | 1.35Y | 7.23 | 0.97 | 1.3 |
| Example 10 | 1.82Y | 7.45 | 1.12 | 1.7 |
| Example 11 | 1.42Y | 7.28 | 0.95 | 1.4 |
| Example 12 | 1.87Y | 7.55 | 1.10 | 1.4 |
| Example 13 | 1.32Y | 7.21 | 0.97 | 1.3 |
| Example 14 | 1.30Y | 7.19 | 0.96 | 1.3 |
| Example 15 | 1.31Y | 7.19 | 0.96 | 1.4 |
| Example 16 | 1.28Y | 7.16 | 0.95 | 1.5 |
| Example 17 | 1.31Y | 7.18 | 0.96 | 1.4 |
| Example 18 | 1.30Y | 7.18 | 0.97 | 1.4 |
| Comparative Example 1 | 4.17Y | 8.05 | 1.24 | 1.4 |
| Comparative Example 2 | 4.18Y | 8.07 | 1.20 | 1.5 |
| Comparative Example 3 | 4.77Y | 8.12 | 2.08 | 1.6 |
| Comparative Example 4 | 2.53Y | 7.88 | 0.86 | 2.0 |
| Comparative Example 5 | 1.93Y | 5.87 | 2.55 | 2.1 |
| Comparative Example 6 | 2.55Y | 7.86 | 0.85 | 2.2 |
| Comparative Example 7 | 1.91Y | 5.87 | 2.54 | 2.3 |
| Comparative Example 8 | 1.94Y | 6.31 | 2.24 | 4.5 |
| Comparative Example 9 | 4.21Y | 8.08 | 1.22 | 1.5 |
| Comparative Example 10 | 4.18Y | 8.06 | 1.21 | 1.5 |

TABLE 6

| | Color Tone Compatibility | | | |
|---|---|---|---|---|
| | Category A | | Category B | |
| Example No. | low-chromaticity model tooth | high-chromaticity model tooth | low-chromaticity model tooth | high-chromaticity model tooth |
| Example 1 | B2 | B2 | A2 | A2 |
| Example 2 | B2 | B1 | A2 | A1 |
| Example 3 | A1 | A2 | B1 | B2 |
| Example 4 | A1 | A1 | B1 | B1 |
| Example 5 | A1 | A1 | B1 | B1 |
| Example 6 | A1 | A1 | B1 | B1 |
| Example 7 | A1 | A2 | B1 | B2 |
| Example 8 | A1 | A1 | B1 | B1 |
| Example 9 | A1 | A1 | B1 | B1 |
| Example 10 | A2 | A2 | B2 | B2 |

TABLE 6-continued

| | Color Tone Compatibility | | | |
|---|---|---|---|---|
| | Category A | | Category B | |
| Example No. | low-chromaticity model tooth | high-chromaticity model tooth | low-chromaticity model tooth | high-chromaticity model tooth |
| Example 11 | A1 | A1 | B1 | B1 |
| Example 12 | A1 | A2 | A1 | A2 |
| Example 13 | A1 | A1 | B1 | B1 |
| Example 14 | A1 | A1 | B1 | B1 |
| Example 15 | A1 | A1 | B1 | A2 |
| Example 16 | A1 | A2 | A1 | A2 |
| Example 17 | A1 | A1 | B1 | B1 |
| Example 18 | A1 | A1 | B1 | A1 |
| Comparative Example 1 | D | D | C | C |
| Comparative Example 2 | D | D | C | C |
| Comparative Example 3 | D | D | D | D |
| Comparative Example 4 | B2 | C | C | D |
| Comparative Example 5 | D | D | D | D |
| Comparative Example 6 | B2 | C | C | D |
| Comparative Example 7 | D | D | D | D |
| Comparative Example 8 | C | B1 | D | D |
| Comparative Example 9 | D | D | D | D |
| Comparative Example 10 | D | D | D | D |

As understood from the results of Examples 1 to 18, the resin block for dental cutting work that satisfies the requirement defined in the present invention can show colored light on a black background and has good color tone compatibility, and further it is known that the color tone change with time of the resin block for dental cutting work obtained in the present invention is small.

As understood from the results of Comparative Examples 1 to 7, 9 and 10, it is known that the colored light from the resin block for dental cutting work not satisfying the requirement defined in the present invention is blueish on a black background (Comparative Examples 1 and 2: average particle size of spherical filler<230 nm, Comparative Examples 9 and 10: refractive index of resin matrix>refractive index of spherical filler), that the resin block does not express colored light (Comparative Example 3: average particle size of spherical filler 80 nm, Comparative Examples 5 and 7: filler is irregularly shaped), that the colored light from the resin block is weak (Comparative Examples 4 and 6: proportion of particles falling within a range of the average particle size of spherical filler±5% is 88%), and that all the resin blocks are poor in color tone compatibility with model teeth.

As understood from the results of Comparative Example 8, it is observed that, when the spectral reflectivity of the resin block for dental cutting work that has been produced by adding a pigment to the composition of Comparative Example 3 so as to have a controlled color tone (a color tone compatible with the category A of high-chromaticity model teeth) is measured on a black background and on a white background using a colorimeter (from Tokyo Denshoku Co., Ltd., "TC-1800MKII"), the resin block shows spectral reflection characteristics on both the black background and the white background depending on the pigment added. The color tone compatibility of the resin block with the color tone corresponding to the category A of high-chromaticity model teeth is high, but the color tone compatibility thereof with other model teeth is poor. Further, the color tone change with time of the resin block is large.

The invention claimed is:

1. A resin block for dental cutting work comprising a resin matrix (A) and a spherical filler (B) whose average particle size falls within a range of 230 nm to 1000 nm,
   wherein the resin block for dental cutting work further comprises inorganic particles (C) having an average particle size of less than 100 nm, and wherein an amount of the inorganic particles (C) is 0.1 to 30 parts by mass relative to 100 parts by mass of the resin matrix (A),
   wherein the resin block for dental cutting work is such that, when having a thickness of 10 mm and measured with a colorimeter, the lightness (V) is less than 5.0 and the saturation (C) is less than 2.0 as measured values in a Munsell color system of a colored light on a black background and a white background, and is such that, when having a thickness of 1 mm and as measured with a colorimeter, the lightness (V) is less than 5.0 and the saturation (C) is 0.05 or more as measured values in a Munsell color system of the colored light on a black background, but on a white background, the lightness (V) is 6.0 or more and the saturation (C) is less than 2.0 as measured values in a Munsell color system of the colored light, wherein 90% or more of the individual particles constituting the spherical filler (B) are present within a range of the average particle size ±5%, and the resin matrix (A) and the spherical filler (B) each are selected so as to satisfy a requirement (X1) represented by the following expression (1):

$$nP < nF \quad (1)$$

where nP represents a refractive index of the resin matrix (A) at 25° C., and nF represents a refractive index of the spherical filler (B) at 25° C.

2. The resin block for dental cutting work according to claim 1, wherein the average particle size of the spherical filler (B) falls within a range of 240 nm to 500 nm.

3. The resin block for dental cutting work according to claim 1, wherein the spherical filler (B) is an inorganic spherical filler (B).

4. The resin block for dental cutting work according to claim 3, comprising an organic-inorganic composite filler (B2) that contains the inorganic spherical filler (B).

5. The resin block for dental cutting work according to claim 4, comprising a powdery spherical filler (B1) consisting of the spherical filler (B), and the organic-inorganic composite filler (B2).

6. A method for producing a resin block for dental cutting work that contains a resin matrix (A) and a spherical filler (B) whose average particle size falls within a range of 230 nm to 1000 nm, wherein the resin block for dental cutting work further comprises inorganic particles (C) having an average particle size of less than 100 nm, and wherein an amount of the inorganic particles (C) is 0.1 to 30 parts by mass, relative to 100 parts by mass of the resin matrix (A); the method comprising polymerizing a curable composition, which contains a polymerizing monomer, a spherical filler (B) whose average particle size falls within a range of 230 nm to 1000 nm, inorganic particles (C) having an average primary particle size of less than 100 nm, and a polymerization initiator, and in which 90% or more of the individual particles constituting the spherical filler (B) are present within a range of the average particle size ±5%, and the polymerizing monomer and the spherical filler (B) each are selected so as to satisfy a requirement (X2) represented by the following expression (2):

$$nPm < nF \qquad (2)$$

where nPm represents a refractive index at 25° C. of a polymer obtained through polymerization of the polymerizing monomer, and nF represents a refractive index of the spherical filler (B) at 25° C.; and wherein the resin block for dental cutting work is such that, when having a thickness of 10 mm and as measured with a colorimeter, the lightness (V) is less than 5.0 and the saturation (C) is less than 2.0 as measured values in a Munsell color system of the colored light on a black background and a white background, and is such that, when having a thickness of 1 mm and as measured with a colorimeter, the lightness (V) is less than 5.0 and the saturation (C) is 0.05 or more as measured values in a Munsell color system of the colored light on a black background, but on a white background, the lightness (V) is 6.0 or more and the saturation (C) is less than 2.0 as measured values in a Munsell color system of the colored light.

* * * * *